US012059305B2

(12) United States Patent
Nishihara

(10) Patent No.: US 12,059,305 B2
(45) Date of Patent: Aug. 13, 2024

(54) ULTRASONIC DIAGNOSTIC DEVICE, MEDICAL IMAGE PROCESSING DEVICE, AND MEDICAL IMAGE PROCESSING METHOD

(71) Applicant: CANON MEDICAL SYSTEMS CORPORATION, Otawara (JP)

(72) Inventor: Kuramitsu Nishihara, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 240 days.

(21) Appl. No.: 16/366,515

(22) Filed: Mar. 27, 2019

(65) Prior Publication Data

US 2019/0298314 A1     Oct. 3, 2019

(30) Foreign Application Priority Data

Mar. 30, 2018   (JP) ................................. 2018-069654

(51) Int. Cl.
*A61B 8/08* (2006.01)
*G01S 7/52* (2006.01)

(52) U.S. Cl.
CPC ............ *A61B 8/5269* (2013.01); *A61B 8/488* (2013.01); *A61B 8/5253* (2013.01); *G01S 7/52095* (2013.01)

(58) Field of Classification Search
CPC ........... A61B 8/5253; A61B 8/06; A61B 8/13; A61B 8/488; A61B 8/0833; A61B 8/145;

(Continued)

(56) References Cited

U.S. PATENT DOCUMENTS 6,814,701 B1 * 11/2004 Tamura ............... G01S 7/52095
                                                                    600/443
2009/0069692 A1 *  3/2009 Cooley ............... G01S 7/52095
                                                                    600/459

(Continued)

FOREIGN PATENT DOCUMENTS

JP          58-138445        8/1983
JP         2012-139256       7/2012

(Continued)

OTHER PUBLICATIONS

Japanese Office Action dated Jan. 4, 2022, issued in Japanese Patent Application No. 2018-069654.

*Primary Examiner* — Keith M Raymond
*Assistant Examiner* — Johnathan Maynard
(74) *Attorney, Agent, or Firm* — Oblon, McClelland, Maier & Neustadt, L.L.P.

(57) ABSTRACT

An ultrasonic diagnostic device according to an embodiment includes reception circuitry and processing circuitry. The reception circuitry outputs a plurality of reception signals corresponding to a plurality of reception scanning lines for each time of transmission/reception of ultrasonic waves performed by an ultrasonic probe. The processing circuitry performs filter processing on each of a plurality of first reception signals output from the reception circuitry based on a first ultrasonic wave transmitted from the ultrasonic probe using at least one specific second reception signal among a plurality of second reception signals output from the reception circuitry based on a second ultrasonic wave the sound field of which is adjacent to or partially overlapped with a sound field of the first ultrasonic wave. The processing circuitry generates image data based on the first reception signals subjected to the filter processing.

13 Claims, 15 Drawing Sheets

(58) Field of Classification Search
CPC ..... A61B 8/4444; A61B 8/483; A61B 8/5207; A61B 8/54; A61B 8/5269; G01S 7/52095; G01S 7/52077; G01S 15/8977; G01S 15/8979; G01S 15/8993; G01S 15/8995; G01S 7/52047; G01S 7/52044; G01S 7/5206; G01S 7/52085; H01F 41/122; H02K 3/34; H02K 3/38

See application file for complete search history.

(56) References Cited

U.S. PATENT DOCUMENTS

| | | | | |
|---|---|---|---|---|
| 2011/0054316 | A1* | 3/2011 | Kristoffersen | G01S 15/8979 600/443 |
| 2015/0245818 | A1* | 9/2015 | Zhai | A61B 8/488 600/453 |
| 2015/0320398 | A1* | 11/2015 | Honjo | A61B 8/5207 600/447 |
| 2018/0203104 | A1* | 7/2018 | Fujii | G01S 7/52095 |

FOREIGN PATENT DOCUMENTS

| | | |
|---|---|---|
| JP | 2015-226762 | 12/2015 |
| JP | 2016-87302 A | 5/2016 |

\* cited by examiner

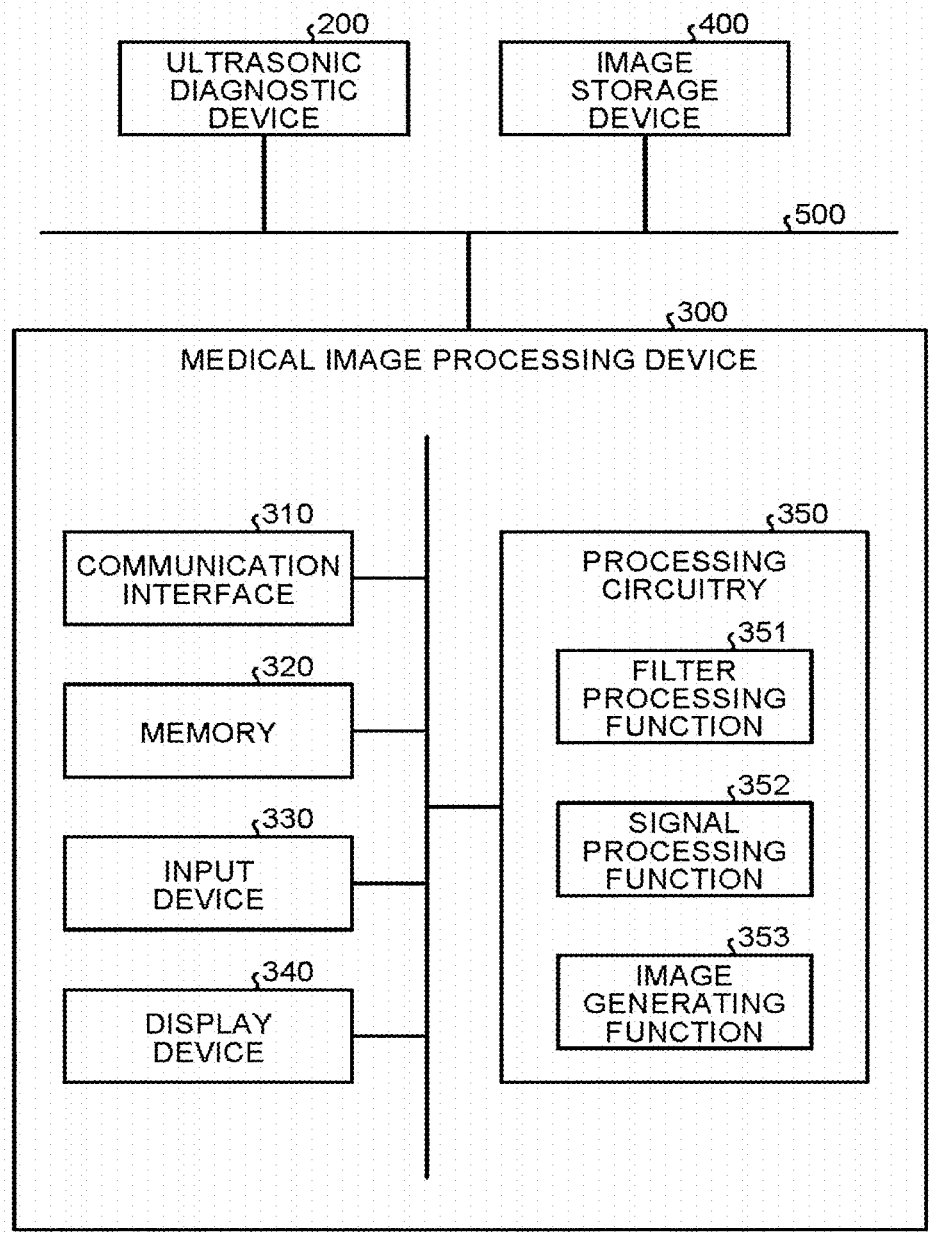

ULTRASONIC DIAGNOSTIC DEVICE, MEDICAL IMAGE PROCESSING DEVICE, AND MEDICAL IMAGE PROCESSING METHOD

CROSS-REFERENCE TO RELATED APPLICATIONS

This application is based upon and claims the benefit of priority from Japanese Patent Application No. 2018-069054, filed on Mar. 30, 2018; the entire contents of which are incorporated herein by reference.

FIELD

Embodiments described herein relate generally to an ultrasonic diagnostic device, a medical image processing device, and a medical image processing method.

BACKGROUND

In the related art, ultrasonic diagnostic devices use imaging methods corresponding to various purposes. For example, an ultrasonic diagnostic device performs parallel signal processing for improving a frame rate (time resolution). The parallel signal processing is a technique of improving the frame rate by setting a plurality of reception scanning lines in a sound field of a transmitted ultrasonic wave, and receiving an ultrasonic signal (reflected wave signal) from each of the reception scanning lines substantially at the same time. That is, the parallel signal processing is a technique of collecting a plurality of reception signals for each time of transmission/reception of the ultrasonic waves. To obtain image data for one frame, the ultrasonic diagnostic device may transmit ultrasonic waves having different sound fields multiple times, and may perform parallel signal processing multiple times.

BRIEF DESCRIPTION OF THE DRAWINGS

FIG. 15 is a diagram for explaining an example of processing performed by filter processing circuitry according to a fifth modification of the first embodiment;

FIG. 17 is a diagram for illustrating a configuration example of a medical image processing device according to a second embodiment.

DETAILED DESCRIPTION

An ultrasonic diagnostic device according to an embodiment includes reception circuitry and processing circuitry. For each time of transmission/reception of ultrasonic waves performed by an ultrasonic probe, the reception circuitry outputs a plurality of reception signals corresponding to a plurality of reception scanning lines. The processing circuitry performs filter processing on each of a plurality of first reception signals output from the reception circuitry based on a first ultrasonic wave transmitted from the ultrasonic probe by using at least one specific second reception signal among a plurality of second reception signals output from the reception circuitry based on a second ultrasonic wave a sound field of which is adjacent to or partially overlapped with a sound field of the first ultrasonic wave. The processing circuitry generates image data based on the first reception signals subjected to filter processing.

The following describes an ultrasonic diagnostic device, a medical image processing device, and a medical image processing method according to embodiments with reference to the drawings. Content described in one of embodiments or modifications may be similarly applied to the other embodiments or the other modifications.

First Embodiment

Figure 1:
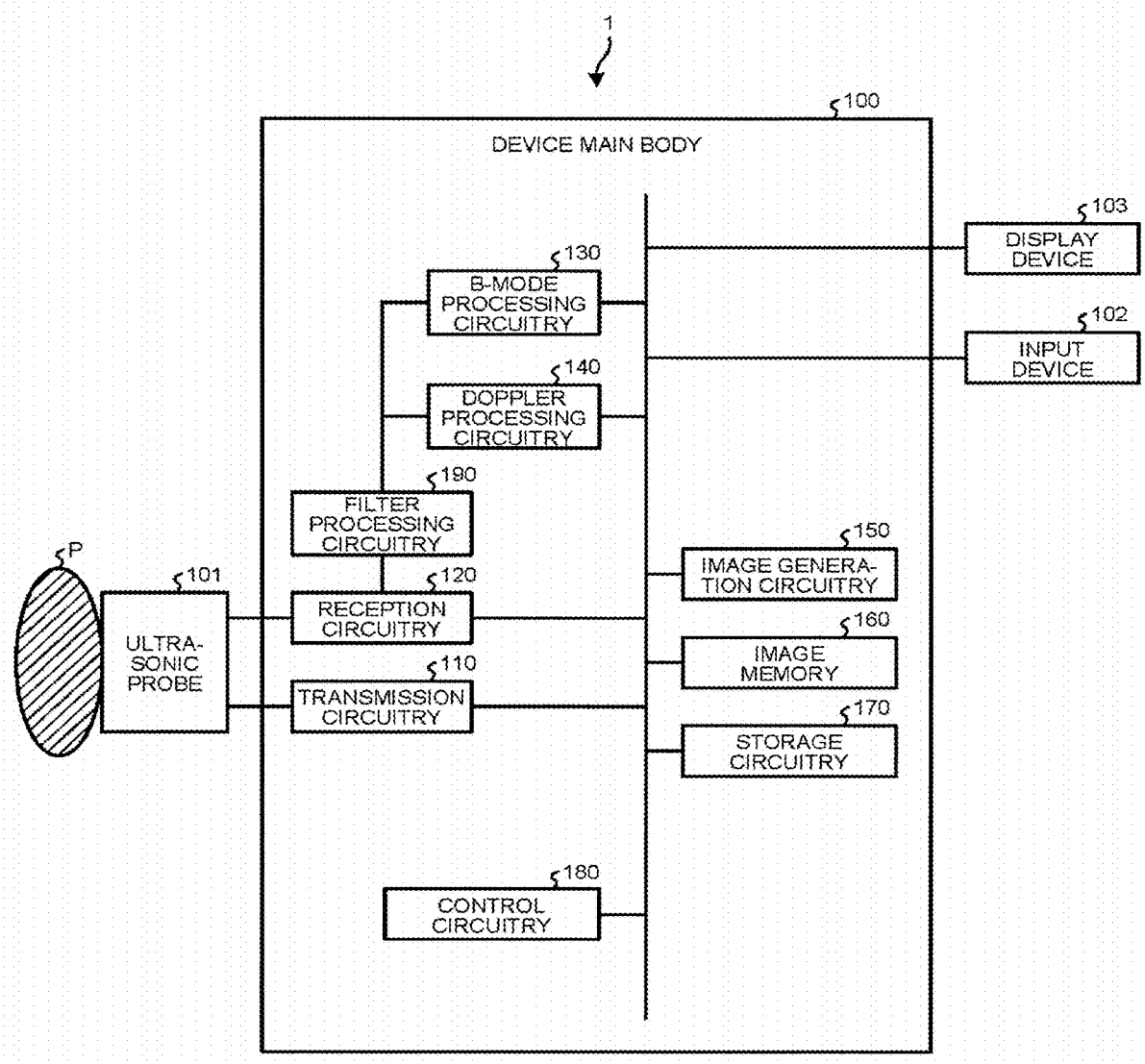
FIG. 1 is a block diagram illustrating a configuration example an ultrasonic diagnostic device according to a first embodiment.

FIG. 1 is a block diagram illustrating a configuration example of an ultrasonic diagnostic device 1 according to a first embodiment. As exemplified in FIG. 1, the ultrasonic diagnostic device 1 according to the first embodiment includes a device main body 100, an ultrasonic probe 101, an input device 102, and a display device 103.

The ultrasonic probe 101 includes, for example, a plurality of elements such as piezoelectric transducer elements. The elements generate ultrasonic waves based on a drive signal supplied from transmission circuitry 110 (described later) included in the device main body 100. The ultrasonic probe 101 receives reflected waves from a subject P, and converts the reflected waves into electric signals. The ultrasonic probe 101 includes, for example, a matching layer disposed in the piezoelectric transducer element, a backing material that prevents ultrasonic waves from backwardly propagating from the piezoelectric transducer element, and the like. The ultrasonic probe 101 is connected to the device main body 100 in a detachable manner.

When ultrasonic waves are transmitted from the ultrasonic probe 101 to the subject P, the transmitted ultrasonic waves are successively reflected by a discontinuity in acoustic impedance in body tissues of the subject P, and received by a plurality of elements included in the ultrasonic probe 101 as reflected waves. Amplitudes of the received reflected waves depend on a difference in acoustic impedance of the discontinuity by which the ultrasonic waves are reflected. In a case in which transmitted ultrasonic pulses are reflected by a surface of a moving blood flow, a cardiac wall, and the like, the reflected waves depend on a velocity component with respect to an ultrasonic wave transmitting direction of a moving object, and are subjected to frequency shift due to the Doppler effect.

The ultrasonic probe 101 is disposed to be detachable from the device main body 100. In a case of performing scanning on a two-dimensional region (two-dimensional scanning) in the subject P, for example, an operator connects a 1D array probe including a plurality of piezoelectric transducer elements arranged in a line to the device main body 100 as the ultrasonic probe 101. Examples of the 1D array probe include a linear ultrasonic probe, a convex ultrasonic probe, and a sector ultrasonic probe. In a case of performing scanning on a three-dimensional region (three-dimensional scanning) in the subject P, for example, the operator connects a mechanical 4D probe or a 2D array probe to the device main body 100 as the ultrasonic probe 101. The mechanical 4D probe can perform two-dimensional scanning by using a plurality of piezoelectric transducer elements arranged in a line such as the 1D array probe, and can also perform three-dimensional scanning by swinging the piezoelectric transducer elements at a predetermined angle (swinging angle). The 2D array probe can perform three-dimensional scanning with a plurality of piezoelectric transducer elements arranged in a matrix, and can also perform two-dimensional scanning by converging ultrasonic waves to be transmitted. The following describes a case in which the 1D array probe is connected to the device main body 100.

The input device 102 is, for example, implemented by an input module such as a mouse, a keyboard, a button, a panel switch, a touch command screen, a foot switch, a trackball, and a joystick. The input device 102 receives various setting requests from the operator of the ultrasonic diagnostic device 1, and transfers the received various setting requests to the device main body 100.

For example, the display device 103 displays a graphical user interface (GUI) through which the operator of the ultrasonic diagnostic device 1 inputs various setting requests using the input device 102, or displays an ultrasonic image and the like indicated by ultrasonic image data generated by the device main body 100. The display device 103 is implemented by a liquid crystal monitor, a cathode ray tube (CRT) monitor, and the like.

The device main body 100 generates ultrasonic image data based on reflected wave signals transmitted from the ultrasonic probe 101. The ultrasonic image data is an example of image data. The device main body 100 can generate two-dimensional ultrasonic image data based on reflected wave signals corresponding to the two-dimensional region of the subject P transmitted from the ultrasonic probe 101. The device main body 100 can also generate three-dimensional ultrasonic image data based on reflected wave signals corresponding to the three-dimensional region of the subject P transmitted from the ultrasonic probe 101. As illustrated in FIG. 1, the device main body 100 includes the transmission circuitry 110, reception circuitry 120, B-mode processing circuitry 130, Doppler processing circuitry 140, image generation circuitry 150, an image memory 160, storage circuitry 170, control circuitry 180, and filter processing circuitry 190.

The transmission circuitry 110 causes the ultrasonic probe 101 to transmit ultrasonic waves. The transmission circuitry 110 includes rate pulser generation circuitry, transmission delay circuitry, and a transmission puller, and supplies a drive signal to the ultrasonic probe 101. In a case of scanning the two-dimensional region in the subject P, the transmission circuitry 110 causes the ultrasonic probe 101 to transmit an ultrasonic beam for scanning the two-dimensional region. In a case of scanning the three-dimensional region in the subject P, the transmission circuitry 110 causes the ultrasonic probe 101 to transmit an ultrasonic beam for scanning the three-dimensional region.

The rate pulser generation circuitry repeatedly generates rate pulses for forming transmission ultrasonic waves (transmission beam) at a predetermined rate frequency (pulse repetition frequency (PRF)). When the rate pulses pass through the transmission delay circuitry, voltage is applied to the transmission pulsar in a state of having different transmission delay times. For example, the transmission delay circuitry gives, to each rate pulse generated by the rate pulser generation circuitry, a transmission delay time for each piezoelectric transducer element required for converging ultrasonic waves generated by the ultrasonic probe 101 in a beam form to determine transmission directivity. The transmission pulsar applies a drive signal (drive pulse) to the ultrasonic probe 101 at a timing based on the rate pulse. The transmission delay circuitry optionally adjusts a transmission direction of the ultrasonic waves from a surface of the piezoelectric transducer element by changing the transmission delay time given to each rate pulse.

After being transmitted from the transmission pulser to the piezoelectric transducer element in the ultrasonic probe 101 via a cable, the drive pulse is converted from the electric signal into mechanical vibration by the piezoelectric transducer element. The ultrasonic waves generated from the mechanical vibration are transmitted to the inside of a living body. The ultrasonic waves having different transmission delay times for each piezoelectric transducer element are converged, and propagate in a predetermined direction.

The transmission circuitry 110 has a function of being able to instantly change a transmission frequency, a transmission driving voltage, and the like to perform a predetermined scanning sequence under control by the control circuitry 180. Specifically, the transmission driving voltage is changed by linear-amplifier type oscillation circuitry that can instantly switch a value of the transmission driving voltage, or a mechanism that electrically switches a plurality of power supply units.

After reaching the piezoelectric transducer element inside the ultrasonic probe 101, the reflected waves of the ultrasonic waves transmitted from the ultrasonic probe 101 are converted from mechanical vibration into electric signals (reflected wave signals) by the piezoelectric transducer element, and input to the reception circuitry 120. The reception circuitry 120 includes a preamplifier, an analog to digital (A/D) converter, quadrature detection circuitry, and the like, performs various kinds of processing on the reflected wave signals transmitted from the ultrasonic probe 101 to generate reflected wave data, and outputs the generated reflected wave data to the filter processing circuitry 190. The reception circuitry 120 generates two-dimensional reflected wave data from two-dimensional reflected wave signals transmitted from the ultrasonic probe 101. The reception circuitry 120 also generates three-dimensional reflected wave data from three-dimensional reflected wave signals transmitted from the ultrasonic probe 101. The reflected wave data is an example of a reception signal. The reception circuitry 120 is an example of a reception unit.

The preamplifier amplifies the reflected wave signal for each channel to perform gain adjustment (gain correction). The A/D converter A/D-converts the gain-corrected reflected wave signal to convert the gain-corrected reflected wave signal into a digital signal. The quadrature detection circuitry converts the A/D-converted reflected wave signal into an in-phase signal (I signal, T: In-phase) and a quadrature-phase signal (Q signal, Q: Quadrature-phase) in a baseband. The quadrature detection circuitry outputs the I signal and the Q signal (IQ signal) to the filter processing circuitry 190 as the reflected wave data. That is, the reflected wave data includes phase information.

The reception circuitry 120 according to the present embodiment can perform parallel signal processing. The parallel signal processing is a technique of improving a frame rate (time resolution) by setting a plurality of reception scanning lines in a sound field of the transmission ultrasonic wave (transmission ultrasonic wave at one time), and receiving ultrasonic signals (reflected wave signals) from the respective reception scanning lines substantially at the same time. That is, the reception circuitry 120 outputs a plurality of pieces of reflected wave data corresponding to a plurality of reception scanning lines for each time of transmission/reception of the ultrasonic waves performed by the ultrasonic probe 101.

In the present embodiment, the reception circuitry 120 performs the parallel signal processing multiple times to obtain the ultrasonic image data for one frame under control by the control circuitry 180. Specifically, in the present embodiment, the transmission circuitry 110 transmits ultrasonic waves having different sound fields multiple times to include the entire scanning range of the ultrasonic image data for one frame, and the reception circuitry 120 performs parallel signal processing every time the ultrasonic waves are transmitted. That is, in the present embodiment, the scanning range of the ultrasonic image data for one frame is divided into a plurality of regions, the transmission circuitry 110 transmits the ultrasonic waves for each region, and the reception circuitry 120 performs parallel signal processing every time the ultrasonic waves are transmitted.

Figure 2:
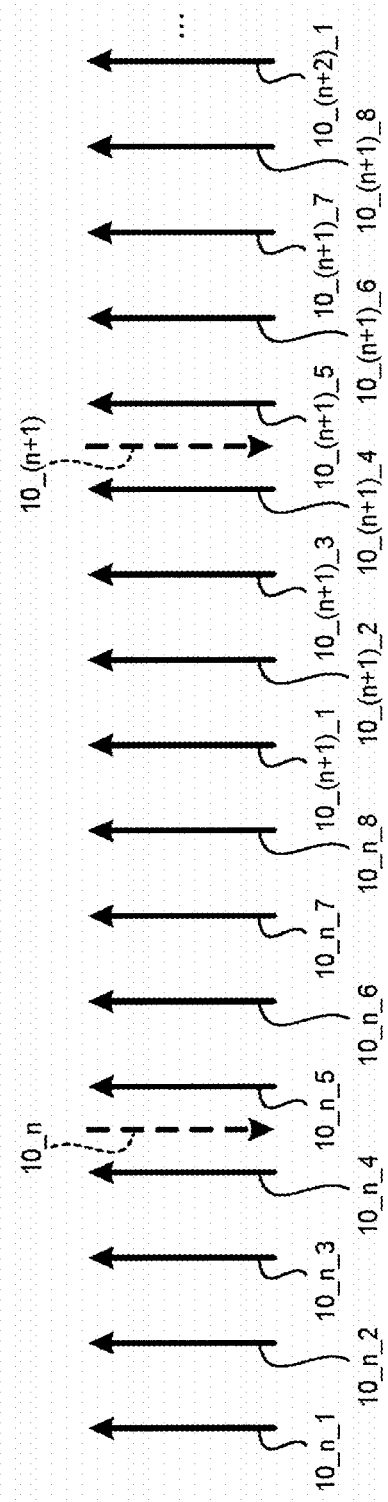
FIG. 2 is a diagram for explaining an example of parallel signal processing that is performed multiple times to obtain ultrasonic image data for one frame according to the first embodiment.

FIG. 2 is a diagram for explaining an example of the parallel signal processing that is performed multiple times to obtain the ultrasonic image data for one frame according to the first embodiment. In the present embodiment, the number of times of parallel signal processing performed for obtaining the ultrasonic image data for one frame is assumed to be M (M is an integral number equal to or larger than 2). That is, to obtain the ultrasonic image data for one frame, the transmission circuitry 110 transmits ultrasonic waves M times.

The present embodiment describes a case in which the reception circuitry 120 sets eight reception scanning lines in the sound field of the transmission ultrasonic wave at one time, and receives the reflected wave signals from the eight reception scanning lines substantially at the same time to generate eight pieces of reflected wave data. That is, the following exemplifies a case in which the number of pieces of reflected wave data generated by the reception circuitry 120 is "8" for one time of parallel signal processing. The number of pieces of reflected wave data generated by the reception circuitry 120 in one time of parallel signal processing is not limited to "8", and may be a different value.

In FIG. 2, the reference numeral "10_$k$ (k is an integral number equal to or larger than 1 and equal to or smaller than M)" indicates an ultrasonic wave transmitted at the k-th time (transmission ultrasonic wave at the k-th time) by the transmission circuitry 110 in obtaining the ultrasonic image data for one frame. The reference numeral "10_$k$_$i$ (i is an integral number equal to or larger than 1 and equal to or smaller than 8)" indicates the i-th reflected wave data generated by the reception circuitry 120 in parallel signal processing at the k-th time.

The i-th reflected wave data generated through the parallel signal processing at the k-th time is generated by the reception circuitry 120 based on the reflected wave signal from the i-th reception scanning line set in the sound field of the transmission ultrasonic wave 10_$k$. In this way, eight pieces of reflected wave data 10_$k$_1 to 10_$k$_8 are generated by the reception circuitry 120 based on the transmission ultrasonic wave 10_$k$ transmitted from the ultrasonic probe 101. That is, the eight pieces of reflected wave data 10_$k$_1 to 10_$k$_8 are pieces of reflected wave data based on the transmission ultrasonic wave 10_$k$.

For example, FIG. 2 illustrates a case in which the transmission circuitry 110 transmits an ultrasonic wave 10_$n$ at the n-th time (n is an integral number equal to or larger than 1 and equal to or smaller than (M−2)), and an ultrasonic wave 10_($n$+1) at the ($n$+1)-th time. As illustrated in FIG. 2, the reception circuitry 120 generates eight pieces of reflected wave data 10_$n$_1 to 10_$n$_8 for one time of transmission of the ultrasonic wave 10_$n$, and outputs the eight pieces of reflected wave data 10_$n$_1 to 10_$n$_8 to the filter processing circuitry 190. Similarly, the reception circuitry 120 transmits eight pieces of reflected wave data 10_($n$+1)_1 to 10_($n$+1)_8 for one time of transmission of the ultrasonic wave 10_($n$+1), and outputs the eight pieces of reflected wave data 10_($n$+1)_1 to 10_($n$+1)_8 to the filter processing circuitry 190.

FIG. 2 also illustrates reflected wave data 10_($n$+2)_1 generated by the reception circuitry 120 for one time of transmission of an ultrasonic wave 10_($n$+2) (not illustrated).

The following describes a positional relation among sound fields in a generalized manner according to the present embodiment. For example, assuming that j is an integral number equal to or larger than 1 and equal to or smaller than (M−1), a sound field of the transmission ultrasonic wave at the j-th time and a sound field of the transmission ultrasonic wave at the ($j$+1)-th time are adjacent to each other. In other words, assuming that p is an integral number equal to or larger than 2 and equal to or smaller than (M−1), a sound field of a transmission ultrasonic wave 10_($p$−1) at the ($p$−1)-th time is present on one end side of a sound field of a transmission ultrasonic wave 10_$p$ at the p-th time. A sound field of a transmission ultrasonic wave 10_($p$+1) at the ($p$+1)-th time is present on the other end side of the sound field of the transmission ultrasonic wave 10_$p$. For example, one end side of the sound field of the transmission ultrasonic wave 10_$p$ indicates a side on which the sound field of the transmission ultrasonic wave 10_1 at the first time is positioned. The other end side of the sound field of the transmission ultrasonic wave 10_*p* indicates, for example, a side on which a sound field of a transmission ultrasonic wave 10_M at the M-th time is positioned.

The following describes arrangement order of (8×M) reception scanning lines that are set in obtaining the ultrasonic image data for one frame. In the following description, "50_*k*_*i*" denotes the i-th reception scanning line set in the sound field of the transmission ultrasonic wave 10_*k* at the k-th time. That is, the reception scanning line 50_*k*_*i* has a correspondence relation with the reflected wave data 10_*k*_*i*.

In the present embodiment, the reception scanning lines are arranged at regular intervals in order of a reception scanning line 50_*k*_1, a reception scanning line 50_*k*_2, . . . , a reception scanning line 50_*k*_7, and a reception scanning line 50_*k*_8 in the sound field of one transmission ultrasonic wave 10_*k* from a reception scanning line 50_1_1 toward a reception scanning line 50_M_8. The sound field of the transmission ultrasonic wave 10_1, the sound field of the transmission ultrasonic wave 10_2, . . . , the sound field of the transmission ultrasonic wave 10_(M−1), and the sound field of the transmission ultrasonic wave 10_M are arranged in this order. Thus, the reception scanning line 50_*k*_8 is adjacent to a reception scanning line 50_(*k*+1)_1, and the reception scanning line 50_*k*_1 is adjacent to a reception scanning line 50_(*k*−1)_8. In this way, the reception circuitry 120 sets the reception scanning lines 50_1_1 to 50_M_8 so that positions of 8×M reception scanning lines 50_1_1 to 50_M_8 are different from each other.

The filter processing circuitry 190 performs filter processing on input data. For example, the filter processing circuitry 190 performs filter processing on the reflected wave data. The filter processing circuitry 190 outputs the reflected wave data subjected to filter processing to the B-mode processing circuitry 130 and the Doppler processing circuitry 140. The filter processing circuitry 190 is, for example, implemented by a processor. The filter processing circuitry 190 is an example of a filter processing unit. Details about the filter processing circuitry 190 will be described later.

The B-mode processing circuitry 130 performs logarithmic amplification, envelope detection processing, logarithmic compression, and the like on the reflected wave data output from the filter processing circuitry 190, and generates data (B-mode data) in which signal intensity (amplitude intensity) for each sample point is represented as a degree of luminance. The B-mode processing circuitry 130 outputs the generated B-mode data to the image generation circuitry 150. The B-mode processing circuitry 130 is, for example, implemented by a processor.

The Doppler processing circuitry 140 performs frequency analysis of the reflected wave data output from the filter processing circuitry 190 to extract motion information of a moving object (blood flow, tissues, a contrast medium echo component, and the like) based on the Doppler effect, and generates data (Doppler data) indicating the extracted motion information. For example, the Doppler processing circuitry 140 extracts an average speed, a variance, power, and the like for multiple points as the motion information of the moving object, and generates the Doppler data indicating the extracted motion information of the moving object. The Doppler processing circuitry 140 outputs the generated Doppler data to the image generation circuitry 150.

Specifically, the Doppler processing circuitry 140 executes a color Doppler method, and performs frequency analysis based on the Doppler effect to extract the motion information of blood flow from a plurality of pieces of reflected wave data based on the ultrasonic waves that are transmitted multiple times in the same direction (on the same scanning line). A data column of the reflected wave signals from the same point of the data obtained by transmitting ultrasonic waves multiple times in the same direction is called a packet. A packet size is, for example, about 5 to 16.

The Doppler processing circuitry 140 applies a wall filter that suppresses a signal from tissues (also referred to as a clutter signal) to the packet, and extracts a signal (blood flow signal) from the blood flow. The Doppler processing circuitry 140 then performs autocorrelation processing of calculating an autocorrelation value (autocorrelation coefficient) by taking a complex conjugate of reflected wave data (IQ signal) of a blood flow signal of the latest frame and reflected wave data of a blood flow signal of a frame previous to the latest frame. For example, the Doppler processing circuitry 140 calculates an autocorrelation value C0 (lag 0) and an autocorrelation value C1 (lag 1). By performing autocorrelation processing of calculating the autocorrelation value, the Doppler processing circuitry 140 merges a plurality of blood flow signals (complex signals) into one complex signal. The Doppler processing circuitry 140 then calculates power, an average speed, and a variance based on the calculated autocorrelation value. For example, the Doppler processing circuitry 140 calculates the power, the average speed, and the variance based on two autocorrelation values of lag 0 and lag 1. The Doppler processing circuitry 140 outputs Doppler data indicating at least one of the average speed, the variance, and the power. The Doppler processing circuitry 140 is, for example, implemented by a processor.

The B-mode processing circuitry 130 and the Doppler processing circuitry 140 can process both of the two-dimensional reflected wave data and the three-dimensional reflected wave data.

The image generation circuitry 150 generates ultrasonic image data from the data output from the B-mode processing circuitry 130 and the Doppler processing circuitry 140. The image generation circuitry 150 is implemented by a processor. Typically, the image generation circuitry 150 converts (scan-converts) a scanning line signal string of ultrasonic scanning into a scanning line signal string in a video format typified by a television and the like, and generates ultrasonic image data for display. For example, the image generation circuitry 150 performs coordinate transformation in accordance with a scanning mode for ultrasonic waves of the ultrasonic probe 101 to generate the ultrasonic image data for display. As various kinds of image processing other than scan-converting, for example, the image generation circuitry 150 performs image processing (smoothing processing) of regenerating a luminance average value image using a plurality of image frames after scan-converting, image processing (edge emphasis processing) using a differential filter within the image, and the like. The image generation circuitry 150 synthesizes the ultrasonic image data with character information of various parameters, graduations, body marks, and the like.

Additionally, the image generation circuitry 150 performs coordinate transformation on three-dimensional B-mode data generated by the B-mode processing circuitry 130 to generate three-dimensional B-mode image data. The image generation circuitry 150 also performs coordinate transformation on three-dimensional Doppler data generated by the Doppler processing circuitry 140 to generate three-dimensional Doppler image data. That is, the image generation circuitry 150 generates "the three-dimensional B-mode image data and the three-dimensional Doppler image data"

as "three-dimensional ultrasonic image data (volume data)". The image generation circuitry 150 performs various kinds of rendering processing on the volume data to generate various kinds of two-dimensional image data for displaying the volume data on the display device 103. The image generation circuitry 150 is an example of a generation unit.

The B-mode data and the Doppler data are ultrasonic image data before scan-conversion processing, and the data generated by the image generation circuitry 150 is ultrasonic image data for display after scan-conversion processing. The B-mode data and the Doppler data are also called raw data.

The image memory 160 is a memory that stores various kinds of image data generated by the image generation circuitry 150. The image memory 160 also stores the data generated by the B-mode processing circuitry 130 and the Doppler processing circuitry 140. The B-mode data and the Doppler data stored in the image memory 160 can be called by the operator after diagnosis, for example, and become the ultrasonic image data for display after passing through the image generation circuitry 150. The image memory 160 also stores the reflected wave data output from the reception circuitry 120. The reflected wave data stored in the image memory 160 is used when the filter processing circuitry 190 performs filter processing. The image memory 160 can also store the reflected wave data subjected to filter processing that is output from the filter processing circuitry 190. For example, the image memory 160 is implemented by a semiconductor memory element such as a random access memory (RAM) and a flash memory, a hard disk, or an optical disc.

The storage circuitry 170 stores a control program for performing transmission/reception of ultrasonic waves, image processing, and display processing, diagnostic information (for example, a patient ID and findings of a doctor), and various kinds of data such as a diagnostic protocol and various body marks. The storage circuitry 170 is also used for storing data stored in the image memory 160 as needed. For example, the storage circuitry 170 is implemented by a semiconductor memory element such as a flash memory, a hard disk, or an optical disc.

The control circuitry 180 controls the entire processing performed by the ultrasonic diagnostic device. Specifically, the control circuitry 180 controls processing performed by the transmission circuitry 110, reception circuitry 120, B-mode processing circuitry 130, the Doppler processing circuitry 140, the image generation circuitry 150, and the filter processing circuitry 190 based on various setting requests input by the operator via the input device 102, and various control programs and various kinds of data read out from the storage circuitry 170. The control circuitry 180 also controls the display device 103 to display an ultrasonic image indicated by the ultrasonic image data for display stored in the image memory 160. The control circuitry 180 is, for example, implemented by a processor. The ultrasonic image is an example of an image.

For example, the word "processor" used in the above description means circuitry such as a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). The processor reads out and executes a program stored in the storage circuitry 170 to implement a function. Instead of storing the program in the storage circuitry 170, the program may be directly incorporated in circuitry of the processor. In this case, the processor reads out and executes the program incorporated in the circuitry to implement the function. Each of the processors according to the present embodiment is not necessarily configured as a single piece of circuitry for each processor, and may be configured as one processor by combining a plurality of independent pieces of circuitry to implement the function. Additionally, a plurality of components in FIG. 1 may be integrated into one processor to implement the function.

The entire configuration of the ultrasonic diagnostic device 1 according to the first embodiment has been described above. The following describes a case of transmitting ultrasonic waves having different sound fields multiple times, and performing parallel signal processing multiple times to obtain the ultrasonic image data for one frame. In this case, in the ultrasonic image indicated by the ultrasonic image data, a streak-like artifact may appear at a portion corresponding to a boundary between two sound fields of ultrasonic waves adjacent to each other. In this case, image quality of the ultrasonic image is deteriorated. Thus, the ultrasonic diagnostic device 1 according to the present embodiment is configured as described below to prevent the image quality of the ultrasonic image from being deteriorated.

Figure 3:
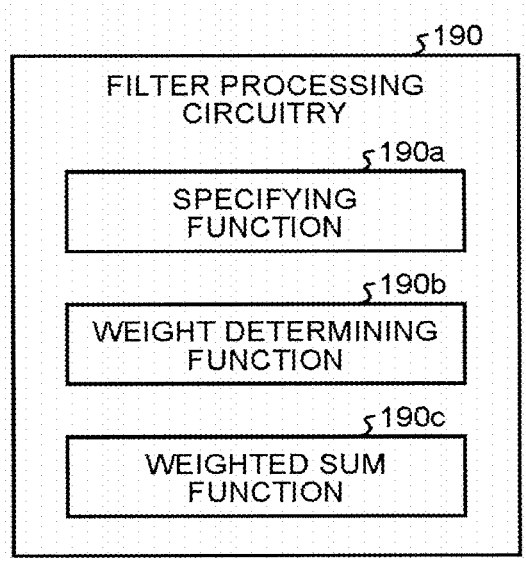
FIG. 3 is a block diagram illustrating a configuration example of filter processing circuitry according to the first embodiment.

FIG. 3 is a block diagram illustrating a configuration example of the filter processing circuitry 190 according to the first embodiment. As illustrated in FIG. 3, the filter processing circuitry 190 has a specifying function 190a, a weight determining function 190b, and weighted sum function 190c.

For example, respective processing functions executed by the specifying function 190a, the weight determining function 190b, and the weighted sum function 190c as the components of the filter processing circuitry 190 illustrated in FIG. 3 are stored in the storage circuitry 170 as computer-executable programs. The filter processing circuitry 190 reads out each of the programs from the storage circuitry 170, and executes each read-out program to implement a function corresponding to the program. In other words, the filter processing circuitry 190 that has read out the programs has the respective functions illustrated in the filter processing circuitry 190 in FIG. 3.

In the present embodiment, each processing function is assumed to be implemented by the single filter processing circuitry 190, but the processing circuitry may be configured by combining a plurality of independent processors, and the functions may be implemented when the respective processors execute the programs.

The storage circuitry 170 may store a program (medical image processing program) for implementing the specifying function 190a, the weight determining function 190b, the weighted sum function 190c, the function of the B-mode processing circuitry 130, the function of the Doppler processing circuitry 140, the function of the image generation circuitry 150, and the function of the control circuitry 180. One processor included in the device main body 100 may read out the medical image processing program, and execute the read-out medical image processing program.

Figure 4:
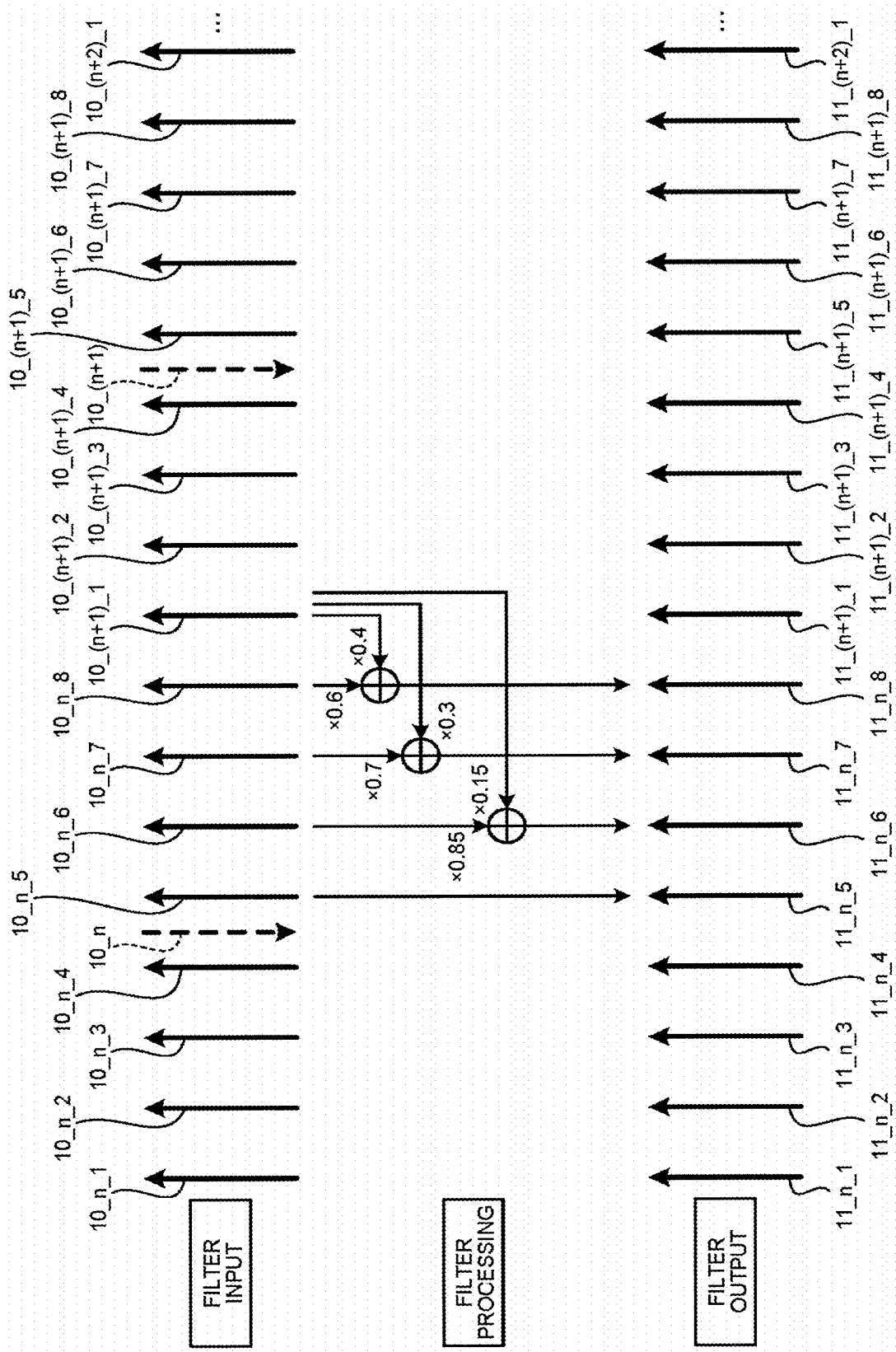
FIG. 4 is a diagram for explaining an example of filter processing performed by the filter processing circuitry according to the first embodiment.
Figure 5:
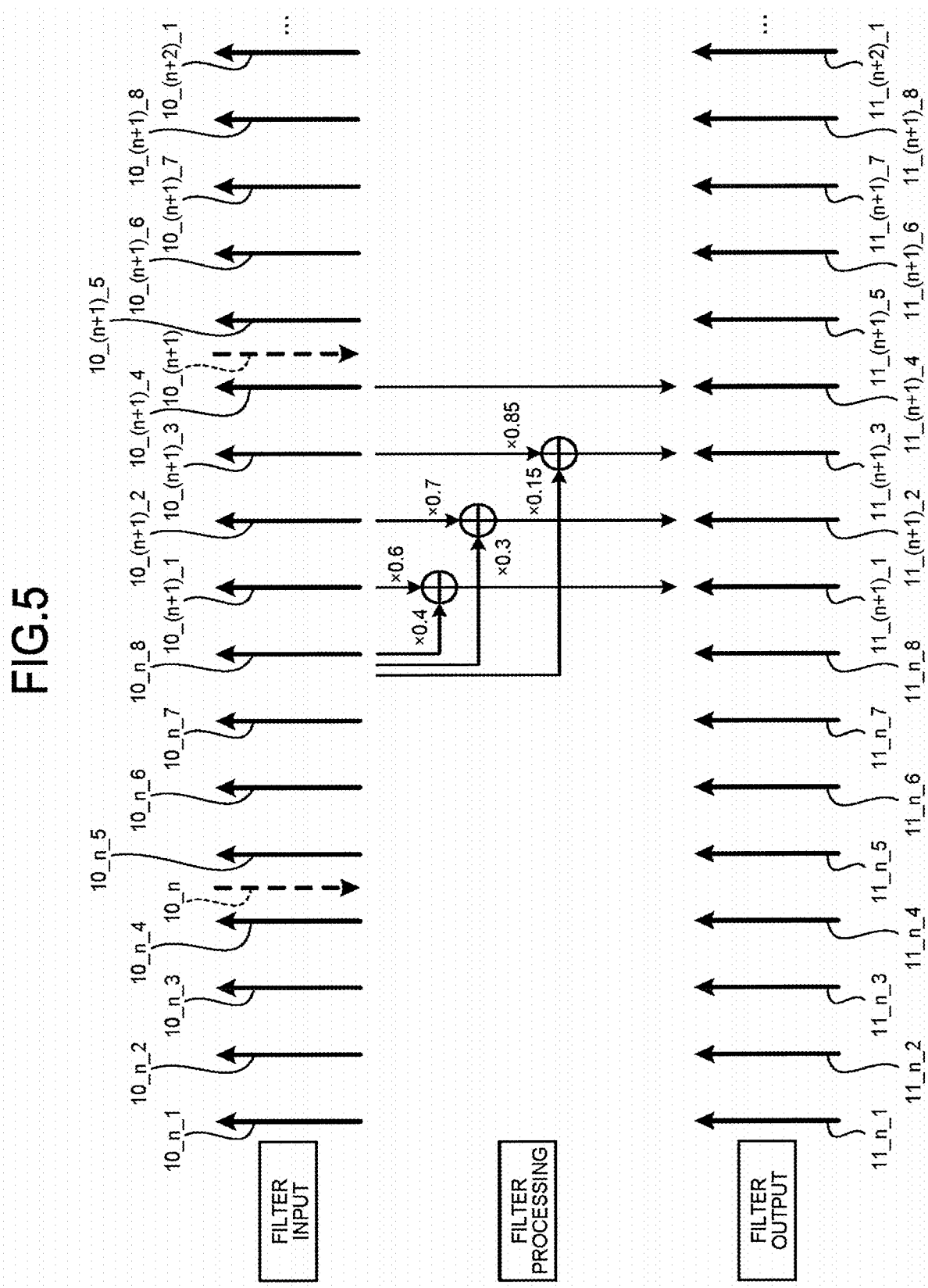
FIG. 5 is a diagram for explaining an example of filter processing performed by the filter processing circuitry according to the first embodiment.

FIG. 4 and FIG. 5 are diagrams for explaining an example of filter processing performed by the filter processing circuitry 190 according to the first embodiment. The filter processing circuitry 190 performs filter processing on pieces of reflected wave data other than the pieces of reflected wave data 10_1_1 to 10_1_4, and 10_M_5 to 10_M_8 (pieces of reflected wave data as processing targets) among all pieces of reflected wave data. Specifically, the filter processing circuitry 190 performs filter processing on each of the I signal and the Q signal included in the pieces of reflected wave data as the processing targets.

FIG. 4 illustrates an example of a case in which the filter processing circuitry 190 performs filter processing on four pieces of reflected wave data 10_*n*_5 to 10_*n*_8 among the pieces of reflected wave data as the processing targets. FIG. 5 illustrates an example of a case in which the filter processing circuitry 190 performs filter processing on four pieces of reflected wave data 10_(*n*+1)_1 to 10_(*n*+1)_4.

In the present embodiment, the filter processing circuitry 190 performs weighted sum processing of weighting and summing the reflected wave data 10_*k_i* and specific reflected wave data corresponding to the reflected wave data 10_*k_i* as filter processing to generate a piece of synthesized data 11_*k_i*. The filter processing circuitry 190 then outputs the synthesized data 11_*k_i* to the B-mode processing circuitry 130 and the Doppler processing circuitry 140 as the reflected wave data 10_*k_i* subjected to filter processing.

First, the following describes the specifying function 190*a* according to the first embodiment. The specifying function 190*a* specifies reflected wave data to be synthesized with the reflected wave data 10_*k_i*. For example, the specifying function 190*a* specifies, as the reflected wave data to be synthesized with the reflected wave data 10_*k_i*, the reflected wave data closest to the reflected wave data 10_*k_i* in arrangement order of the reception scanning lines among a plurality of pieces of reflected wave data based on transmission ultrasonic waves other than the transmission ultrasonic wave at the k-th time.

More specifically, assuming that s is an integral number equal to or larger than 1 and equal to or smaller than 7, the specifying function 190*a* specifies reflected wave data 10_(*s*+1)_1 as the reflected wave data to be synthesized with each of the pieces of reflected wave data 10_*s*_5 to 10_*s*_8. This is because a reception scanning line 50_(*s*+1)_1 (not illustrated) is the closest to each of reception scanning lines 50_*s*_5 to 50_*s*_8 (not illustrated) corresponding to the respective pieces of reflected wave data 10_*s*_5 to 10_*s*_8 in arrangement order of the reception scanning lines. Specifically, the reception scanning line 50_(*s*+1)_1 not illustrated) corresponding to the reflected wave data 10_(*s*+1)_1 is the closest to each of the pieces of reflected wave data 10_*s*_5 to 10_*s*_8 in arrangement order of the reception scanning lines among the reception scanning lines set in the sound fields of transmission ultrasonic waves other than the transmission ultrasonic wave 10_*s* at the s-th time.

In specifying the reflected wave data closest to each of the pieces of reflected wave data 10_*s*_5 to 10_*s*_8, the specifying function 190*a* does not necessarily calculate a distance between each of the reception scanning lines 50_*s*_5 to 50_*s*_8 and all reception scanning lines set in the sound fields of transmission ultrasonic waves other than the transmission ultrasonic wave 10_*s* at the s-th time. For example, the specifying function 190*a* specifies a transmission ultrasonic wave 10_(*s*+1) close to the reception scanning lines 50_*s*_5 to 50_*s*_8 of two transmission ultrasonic waves 10_(*s*−1) and 10_(*s*+1) the sound fields of which are adjacent the sound field of the transmission ultrasonic wave 10_*s*. The specifying function 190*a* may specify the reflected wave data by calculating a distance between each of the reception scanning lines 50_*s*_5 to 50_*s*_8 and each of the reception scanning lines 50_(*s*+1)_1 to 50_(*s*+1)_8 set in the sound field of the transmission ultrasonic wave 10_(*s*+1).

For example, in a case illustrated in FIG. 4, the specifying function 190*a* specifies the reflected wave data 10_(*n*+1)_1 as the reflected wave data to be synthesized with each of the pieces of reflected wave data 10_*n*5 to 10_*n*_8.

Assuming that is an integral number equal to or larger than 2 and equal to or smaller than 8, the specifying function 190*a* specifies reflected wave data 10_(*r*−1)_8 as the reflected wave data to be synthesized with pieces of reflected wave data 10_*r*_1 to 10_*r*_4. This is because a reception scanning line 50_(*r*−1)_8 (not illustrated) is the closest to each of reception scanning lines 50_*r*_1 to 50_*r*_4 (not illustrated) corresponding to the respective pieces of reflected wave data 10_*r*_1 to 10_*r*_4 in arrangement order of the reception scanning lines. Specifically, the reception scanning line 50_(*r*−1)_8 corresponding to the reflected wave data 10_(*r*−1)_8 is the closest to each of the reception scanning lines 50_*r*_1 to 50_*r*_4 (not illustrated) among the reception scanning lines set in the sound fields of transmission ultrasonic waves other than a transmission ultrasonic wave 10_*r* at the r-th time.

In specifying the reflected wave data closest to each of the pieces of reflected wave data 10_*r*_1 to 10_*r*_4, the specifying function 190*a* does not necessarily calculate a distance between each of the reception scanning lines 50_*r*_1 to 50_*r*_4 and all reception scanning lines set in the sound fields of transmission ultrasonic waves other than the transmission ultrasonic wave 10_*r* at the r-th time. For example, the specifying function 190*a* specifies a transmission ultrasonic wave 10_(*r*−1) close to the reception scanning lines 50_*r*_1 to 50_*r*_4 of too transmission ultrasonic waves 10_(*r*−1) and 10_(*r*+1) the sound fields of which are adjacent the sound field of the transmission ultrasonic wave 10_*r*. The specifying function 190*a* may specify the reflected wave data by calculating a distance between each of the reception scanning lines 50_*r*_1 to 50_*r*_8 and each of the reception scanning lines 50_(*r*−1)_1 to 50_(*r*−1)_8 set in the sound field of the transmission ultrasonic wave 10_(*r*−1).

For example, in a case illustrated in FIG. 5, the specifying function 190*a* specifies reflected wave data 10_(*n*−1)_8 as the reflected wave data to be synthesized with each of the pieces of reflected wave data 10_(*n*+1)_1 to 10_(*n*+1)_4.

The reflected wave data specified by the specifying function 190*a* is an example of specific reflected wave data.

Next, the following describes the weight determining function 190*b*. The weight determining function 190*b* determines a weight w1 and a weight w2 used for weighted sum. The weight w1 is a weight for the reflected wave data 10_*k_i* to be subjected to filter processing. The weight w2 is a weight for the specific reflected wave data specified by the specifying function 190*a*. The sum of the weight w1 and the weight w2 (w1+w2) is "1".

The weight determining function 190*b* determines the weight w1 and the weight w2 in accordance with a distance between the reflected wave data 10_*k_i* and the specific reflected wave data for each piece of the reflected wave data 10_*k_i* subjected to filter processing. The distance herein is obtained in arrangement order of the reception scanning lines. For example, the weight determining function 190*b* determines the distance to be shorter as the arrangement order is closer. The weight determining function 190*b* then determines the weight w1 and the weight w2 so that the weight w1 becomes smaller as the distance is shorter.

For example, in a case illustrated in FIG. 4, the weight determining function 190*b* determines the weight w1 for the reflected wave data 10_*n*_8 to be "0.6", and determines the weight w2 for the reflected wave data 10_(*n*+1)_1 to be "0.4". The weight determining function 190*b* also determines the weight w1 for the reflected wave data 10_*n*_7 to be "0.7", and determines the weight w2 for the reflected wave data 10_(n+1)_1 to be "0.3". The reason why the weight w1 for the reflected wave data 10_n_8 is smaller than the weight w1 for the reflected wave data 10_n_7 is as follows. That is, in the arrangement order of the reception scanning lines, the reception scanning line 50_n_8 (not illustrated) corresponding to the reflected wave data 10_n_8 is closer to the reception scanning line 50_(n+1)_1 (not illustrated) corresponding to the specific reflected wave data 10_(n+1)_1 than the reception scanning line 50_n_7 (not illustrated) corresponding to the reflected wave data 10_n_7.

For the same reason, the weight determining function 190b determines the weight w1 for the reflected wave data 10_n_6 to be "0.85", and determines the weight w2 for the reflected wave data 10_(n+1)_1 to be "0.15". The weight determining function 190b also determines the weight w1 for the reflected wave data 10_n_5 to be "1.0", and determines the weight w2 for the reflected wave data 10_(n+1)_1 to be "0".

In a case illustrated in FIG. 5, similarly, the weight determining function 190b determines the weight w1 for the reflected wave data 10_(n+1)_1 to be "0.6", and determines the weight w2 for the reflected wave data 10_n_8 to be "0.4". The weight determining function 190b also determines the weight w1 for the reflected wave data 10_(n+1)_2 to be "0.7", and determines the weight w2 for the reflected wave data 10_n_8 to be "0.3".

The weight determining function 190b determines the weight w1 for the reflected wave data 10_(n+1)_3 to be "0.85", and determines the weight w2 for the reflected wave data 10_n_8 to be "0.15". The weight determining function 190b also determines the weight w1 for the reflected wave data 10_(n+1)_4 to be "1.0", and determines the weight w2 for the reflected wave data 10_n_8 to be "0".

Next, the following describes the weighted sum function 190c. The weighted sum function 190c weights and sums the reflected wave data 10_k_i and the specific reflected wave data corresponding to the reflected wave data 10_k_i using the weight w1 and the weight w2 determined by the weight determining function 190b for each piece of the reflected wave data 10_k_i as the processing target. Specifically, as represented by the following expression (1), the weighted sum function 190c weights and sums the reflected wave data 10_k_i and the reflected wave data specified by the specifying function 190a to generate synthesized data 11_k_i.

$$\text{synthesized data } 11\_k\_i = \text{reflected wave data } 10\_k\_i \times w1 + \text{specified reflected wave data} \times w2 \quad (1)$$

For example, in a case illustrated in FIG. 4, the weighted sum function 190c synthesizes (sums) data obtained by multiplying the reflected wave data 10_n_8 by the weight "0.6" and data obtained by multiplying the reflected wave data 10_(n+1)_1 by the weight "0.4" to generate synthesized data 11_n_8.

The weighted sum function 190c synthesizes data obtained by multiplying the reflected wave data 10_n_7 by the weight "0.7" and data obtained by multiplying the reflected wave data 10_(n+1)_1 by the weight "0.3" to generate synthesized data 11_n_7. The weighted sum function 190c synthesizes data obtained by multiplying the reflected wave data 10_n_6 by the weight "0.85" and data obtained by multiplying the reflected wave data 10_(n+1)_1 by the weight "0.15" to generate synthesized data 11_n_6.

The weighted sum function 190c synthesizes data obtained by multiplying the reflected wave data 10_n_5 by the weight "1.0" and data obtained by multiplying the reflected wave data 10_(n+1)_1 by the weight "0" to generate synthesized data 11_n_5. That is, the weighted sum function 190c causes the reflected wave data 10_n_5 to be the synthesized data 11_n_5.

In a case illustrated in FIG. 5, the weighted sum function 190c synthesizes data obtained by multiplying the reflected wave data 10_(n+1)_1 by the weight "0.6" and data obtained by multiplying the reflected wave data 10_n_8 by the weight "0.4" to generate synthesized data 11_(n+1)_1.

The weighted sum function 190c synthesizes data obtained by multiplying the reflected wave data 10_(n+1)_2 by the weight "0.7" and data obtained by multiplying the reflected wave data 10_n_8 by the weight "0.3" to generate synthesized data 11_(n+1)_2. The weighted sum function 190c synthesizes data obtained by multiplying the reflected wave data 10_(n+1)_3 by the weight "0.85" and data obtained by multiplying the reflected wave data 10_n_8 by the weight "0.15" to generate synthesized data 11_(n+1)_3.

The weighted sum function 190c synthesizes data obtained by multiplying the reflected wave data 10_(n+1)_4 by the weight "1.0" and data obtained by multiplying the reflected wave data 10_n_8 by the weight "0" to generate synthesized data 11_(n+1)_4. That is, the weighted sum function 190c causes the reflected wave data 10_(n+1)_4 to be the synthesized data 11_(n+1)_4.

The filter processing circuitry 190 performs the filter processing described above on all pieces of the reflected wave data as the processing targets. As described above, assuming that p is an integral number equal to or larger than 2 and equal to or smaller than (M−1), the processing performed by the reception circuitry 120 and the filter processing circuitry 190 is generalized as described below.

First, the following describes a case in which the filter processing is performed on a plurality of pieces of reflected wave data 10_p_1 to 10_p_8. In this case, for example, the reception circuitry 120 outputs the pieces of reflected wave data 10_p_1 to 10_p_8 corresponding to a plurality of reception scanning lines 50_p_1 to 50_p_8 (not illustrated) through transmission/reception of the transmission ultrasonic wave 10_p. The reception circuitry 120 also outputs a plurality of pieces of reflected wave data 10_(p−1)_1 to 10_(p−1)_8 corresponding to a plurality of reception scanning lines 50_(p−1)_1 to 50_(p−1)_8 (not illustrated) through transmission/reception of the transmission ultrasonic wave 10_(p−1). The reception circuitry 120 also outputs a plurality of pieces of reflected wave data 10_(p+1)_1 to 10_(p+1)_8 corresponding to a plurality of reception scanning lines 50_(p+1)_1 to 50_(p+1)_8 (not illustrated) through transmission/reception of the transmission ultrasonic wave 10_(p+1).

The filter processing circuitry 190 performs filter processing on each of the pieces of reflected wave data 10_p_1 to 10_p_8 using the specific reflected wave data 10_(p−1)_8 or the specific reflected wave data 10_(p+1)_1.

Specifically, first, the filter processing circuitry 190 specifies the reflected wave data to be synthesized with each of the pieces of reflected wave data 10_p_1 to 10_p_4 as follows. For example, the specifying function 190a of the filter processing circuitry 190 specifies the reception scanning line 50_(p−1)_8 closest to each of the reception scanning lines 50_p_1 to 50_p_4 corresponding to the respective pieces of reflected wave data 10_p_1 to 10_p_4 among the reception scanning lines 50_(p−1)_1 to 50_(p−1)_8 (not illustrated). The filter processing circuitry 190 then specifies the reflected wave data 10_(p−1)_8 corresponding to the specified reception scanning line 50_(p−1)_8. The filter processing circuitry 190 performs filter processing on each of the pieces of reflected wave data 10_p_1 to 10_p_4 using the specific reflected wave data 10_(p−1)_8.

The filter processing circuitry 190 specifies the reflected wave data to be synthesized with each of the pieces of reflected wave data 10_p_5 to 10_p_8 as follows. For example, the filter processing circuitry 190 specifies the reception scanning line 50_(p+1)_1 closest to each of the reception scanning lines 50_p_5 to 50_p_8 corresponding to the respective pieces of reflected wave data 10_p_5 to 10_p_8 among the reception scanning lines 50_(p+1)_1 to 50_(p+1)_8 (not illustrated). The filter processing circuitry 190 then specifies the reflected wave data 10_(p+1)_1 corresponding to the specified reception scanning line 50_(p+1)_1. The filter processing circuitry 190 performs filter processing on each of the pieces of reflected wave data 10_p_5 to 10_p_8 using the specific reflected wave data 10_(p+1)_1.

The transmission ultrasonic wave 10_p is an example of the first ultrasonic wave. Each of the transmission ultrasonic wave 10_(p−1) and the transmission ultrasonic wave 10_(p+1) is an example of the second ultrasonic wave. Each of the pieces of reflected wave data 10_p_1 to 10_p_8 is an example of the first reception signal. Each of the pieces of reflected wave data 10_(p−1)_1 to 10_(p−1)_8 and 10_(p+1)_1 to 10_(p+1)_8 is an example of the second reception signal. Each of a plurality of reception scanning lines 50_p_i (not illustrated) is an example of a first reception scanning line. Each of a plurality of reception scanning lines 50_(p−1)_1 to 50_(p−1)_8 and 50_(p+1)_1 to 50_(p+1)_8 is an example of a second reception scanning line. The reception scanning lines 50_p_1 to 50_p_8 and the reception scanning lines 50_(p−1)_1 to 50_(p−1)_8 and 50_(p+1)_1 to 50_(p+1)_8 are set at different positions by the reception circuitry 120.

Next, the following describes a case in which filter processing is performed on a plurality of pieces of reflected wave data 10_1_5 to 10_1_8. In this case, the reception circuitry 120 outputs the pieces of reflected wave data 10_1_5 to 10_1_8 corresponding to a plurality of reception scanning lines 50_1_5 to 50_1_8 (not illustrated) through transmission/reception of the transmission ultrasonic wave 10_1 at the first time. The reception circuitry 120 also outputs a plurality of pieces of reflected wave data 10_2_1 to 10_2_8 corresponding to a plurality of reception scanning lines 50_2_1 to 50_2_8 (not illustrated) through transmission/reception of the transmission ultrasonic wave 10_2 at the second time.

The filter processing circuitry 190 specifies the reflected wave data to be synthesized with each of the pieces of reflected wave data 10_1_5 to 10_1_8 as follows. For example, the filter processing circuitry 190 specifies the reception scanning line 50_2_1 closest to each of the reception scanning lines 50_1_5 to 50_1_8 corresponding to the respective pieces of reflected wave data 10_1_5 to 10_1_8 among the reception scanning lines 50_2_1 to 50_2_8 (not illustrated). The filter processing circuitry 190 then specifies the reflected wave data 10_2_1 corresponding to the specified reception scanning line 50_2_1. The filter processing circuitry 190 performs filter processing on each of the pieces of reflected wave data 10_1_5 to 10_1_8 using the specific reflected wave data 10_2_1.

The transmission ultrasonic wave 10_1 is an example of the first ultrasonic wave. The transmission ultrasonic wave 10_2 is an example of the second ultrasonic wave. Each of the pieces of reflected wave data 10_1_5 to 10_1_8 is an example of the first reception signal. Each of the pieces of reflected wave data 10_2_1 to 10_2_8 is an example of the second reception signal. Each of the reception scanning lines 50_1_5 to 50_1_8 is an example of the first reception scanning line. Each of the reception scanning lines 50_2_1 to 50_2_8 is an example of the second reception scanning line.

Next, the following describes a case in which filter processing is performed on a plurality of pieces of reflected wave data 10_M_1 to 10_M_4. The reception circuitry 120 outputs a plurality of pieces of reflected wave data 10_(M−1)_1 to 10_(M−1)_8 corresponding to a plurality of reception scanning lines 50_(M−1)_1 to 50_(M−1)_8 (not illustrated) through transmission/reception of the transmission ultrasonic wave 10_(M−1) at the (M−1)-th time. The reception circuitry 120 also outputs the pieces of reflected wave data 10_M_1 to 10_M_4 corresponding to a plurality of reception scanning lines 50_M_1 to 50_M_4 (not illustrated) through transmission/reception of the transmission ultrasonic wave 10_M at the M-th time.

The filter processing circuitry 190 then specifies the reflected wave data to be synthesized with each of the pieces of reflected wave data 10_M_1 to 10_M_4 as follows. For example, the filter processing circuitry 190 specifies the reception scanning line 50_(M−1)_8 closest to each of the reception scanning lines 50_M_1 to 50_M_4 corresponding to the respective pieces of reflected wave data 10_M_1 to 10_M_4 among the reception scanning lines 50_(M−1)_1 to 50_(M−1)_8 (not illustrated). The filter processing circuitry 190 then specifies the reflected wave data 10_(M−1)_8 corresponding to the specified reception scanning line 50_(M−1)_8. The filter processing circuitry 190 performs filter processing on each of the pieces of reflected wave data 10_M_1 to 10_M_4 using the specific reflected wave data 10_(M−1)_8.

The transmission ultrasonic wave 10_M is an example of the first ultrasonic wave. The transmission ultrasonic wave 10_(M−1) is an example of the second ultrasonic wave. Each of the pieces of reflected wave data 10_M_1 to 10_M_4 is an example of the first reception signal. Each of the pieces of reflected wave data 10_(M−1)_1 to 10_(M−1)_8 is an example of the second reception signal. Each of the reception scanning lines 50_M_1 to 50_M_4 is an example of the first reception scanning line. Each of e reception scanning lines 50_(M−1)_1 to 50_(M−1)_8 is an example of the second reception scanning line.

The filter processing circuitry 190 does not perform filter processing on each of the pieces of reflected wave data 10_1_1 to 10_1_4 based on the transmission ultrasonic wave 10_1 at the first time. Similarly, the filter processing circuitry 190 does not perform filter processing on each of the pieces of reflected wave data 10_M_5 to 10_M_8 based on the transmission ultrasonic wave 10_M at the M-th time.

Figure 6:
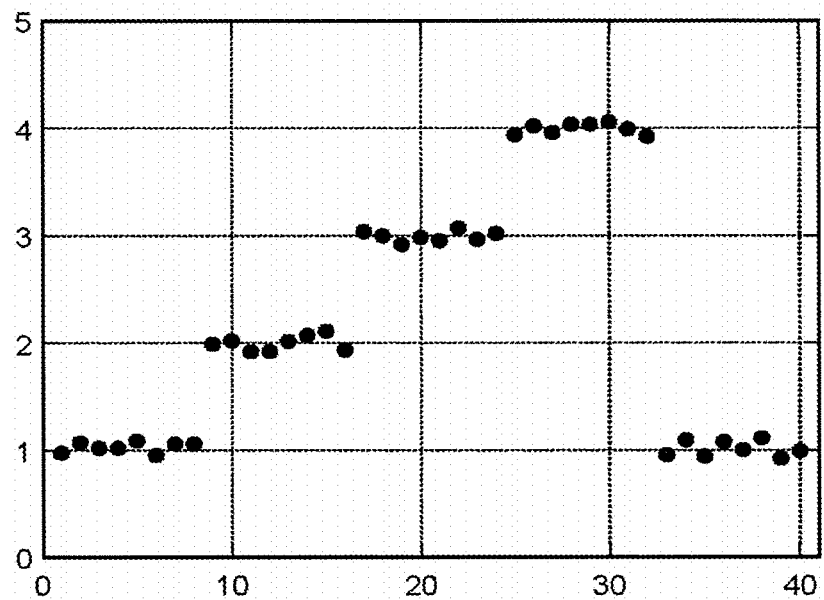
FIG. 6 is a graph illustrating signal intensity of reflected wave data that is artificially created to be input to the filter processing circuitry.
Figure 7:
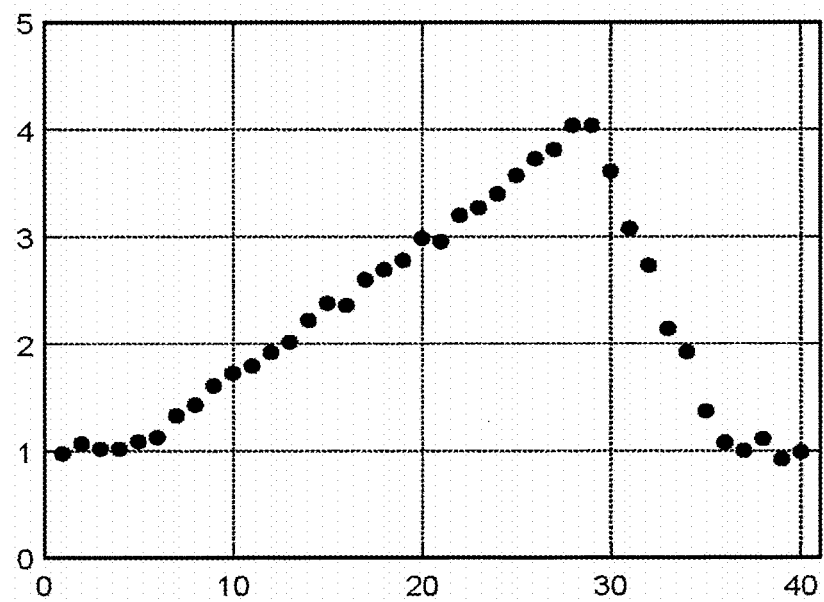
FIG. 7 is a graph illustrating an example of a result obtained when the filter processing circuitry performs filter processing on the reflected wave data illustrated in the graph of FIG. 6.
Figure 8:
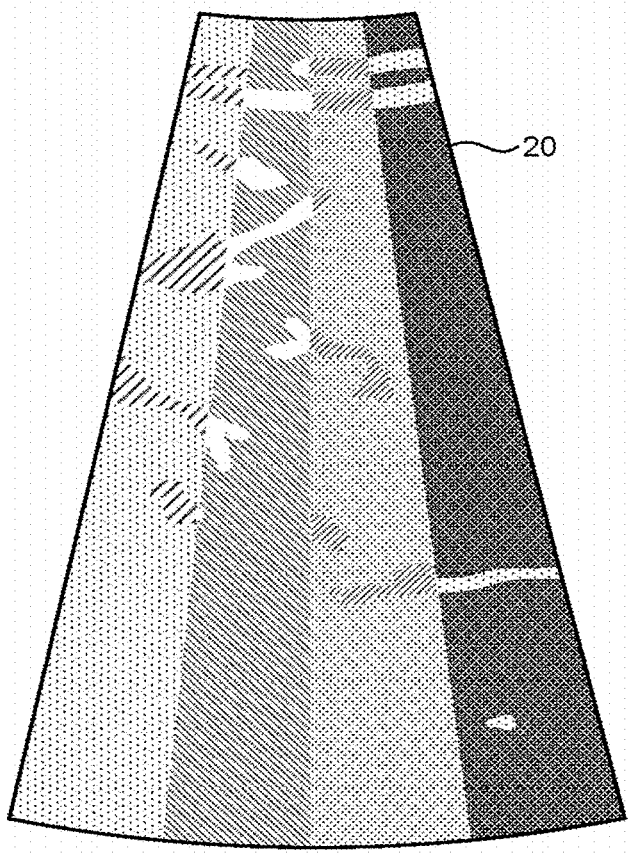
FIG. 8 is a diagram illustrating an example of an ultrasonic image indicated by ultrasonic image data that is generated from 40 pieces of reflected wave data illustrated in the graph of FIG. 6.
Figure 9:
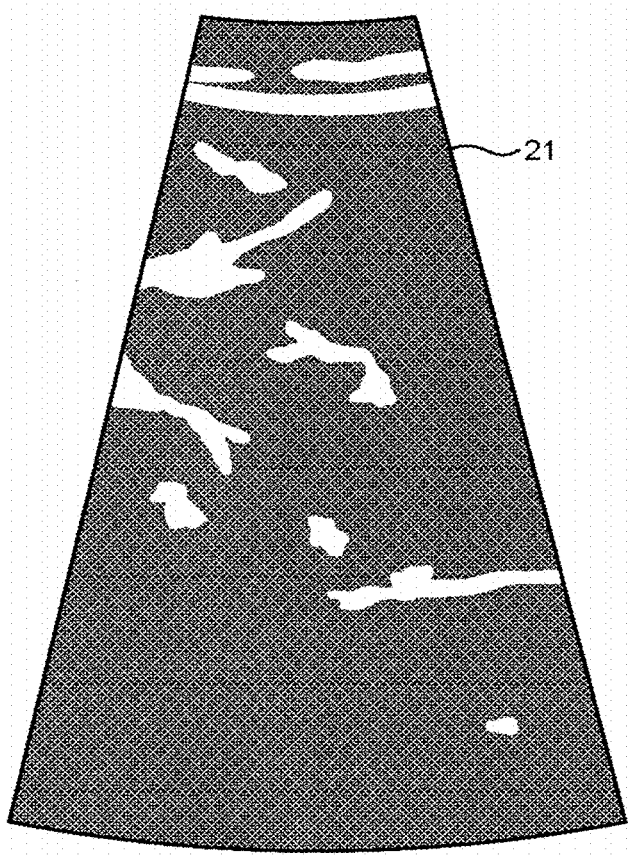
FIG. 9 is a diagram illustrating an example of an ultrasonic image indicated by ultrasonic image data that is generated from 40 pieces of reflected wave data subjected to filter processing illustrated in the graph of FIG. 7.

FIG. 6 is a graph illustrating signal intensity (signal intensity) of the reflected wave data that is artificially created to be input to the filter processing circuitry 190. FIG. 7 is a graph illustrating an example of a result obtained when the filter processing circuitry 190 performs filter processing on the reflected wave data illustrated in the graph of FIG. 6. FIG. 8 is a diagram illustrating an example of an ultrasonic image 20 indicated by ultrasonic image data that is generated from 40 pieces of reflected wave data illustrated in the graph of FIG. 6. FIG. 9 is a diagram illustrating an example of an ultrasonic image 21 indicated by ultrasonic image data that is generated from 40 pieces of reflected wave data subjected to filter processing illustrated in the graph of FIG. 7. The reflected wave data indicated by the graph of FIG. 6 is data of a case in which the number of times of parallel signal processing that is performed to obtain the ultrasonic image data for one frame is "5", and the number of pieces of reflected wave data generated by the reception circuitry 120 through one time of parallel signal processing is "8". Thus, the number of pieces of reflected wave data is "40 (8×5)".

The graph of FIG. 6 is represented by a step function. In the graph of FIG. 6, the horizontal axis indicates arrangement order of the reception scanning lines corresponding to the respective pieces of reflected wave data, and the vertical axis indicates signal intensity of each of the pieces of reflected wave data. In the following description, the reflected wave data corresponding to the e-th (e is an integral number equal to or larger than 1 and equal to or smaller than 40) reception scanning line in arrangement order is represented as "reflected wave data e" in some cases.

As illustrated in the graph of FIG. 6, random noise of ±0.2 at the maximum with respect to "1" is given to the signal intensity of the pieces of reflected wave data 1 to 8 based on the transmission ultrasonic wave at the first time. Similarly, random noise of ±0.2 at the maximum with respect to "2" is given to the signal intensity of the pieces of reflected wave data 9 to 16 based on the transmission ultrasonic wave at the second time. Random noise of ±0.2 at the maximum with respect to "3" is given to the signal intensity of the pieces of reflected wave data 17 to 24 based on the transmission ultrasonic wave at the third time. Random noise of ±0.2 at the maximum with respect to "4" is given to the signal intensity of the pieces of reflected wave data 25 to 32 based on the transmission ultrasonic wave at the fourth time. Random noise of ±0.2 at the maximum with respect to "1" is given to the signal intensity of the pieces of reflected wave data 33 to 40 based on the transmission ultrasonic wave at the fifth time.

In the graph of FIG. 6, for example, a difference in signal intensity is large between the reflected wave data 8 and the reflected wave data 9, between the reflected wave data 16 and the reflected wave data 17, between the reflected wave data 24 and the reflected wave data 25, and between the reflected wave data 32 and the reflected wave data 33. In this way, of the two transmission ultrasonic waves the sound fields of which are adjacent to each other, the signal intensity of the reflected wave data based on one of the transmission ultrasonic waves is largely different from the signal intensity of the reflected wave data based on the other one of the transmission ultrasonic waves at the boundary between the sound fields of the two transmission ultrasonic waves. Thus, as illustrated in FIG. 8, in the ultrasonic image 20 indicated by the ultrasonic image data generated from the 40 pieces of reflected wave data illustrated in the graph of FIG. 6, a streak-like artifact may appear at a portion corresponding to the boundary between the sound fields of the two adjacent ultrasonic waves.

FIG. 7 illustrates an example of a result obtained when the filter processing circuitry 190 performs filter processing on the reflected wave data illustrated in the graph of FIG. 6. In the graph of FIG. 7, the horizontal axis indicates the arrangement order of the reception scanning lines corresponding to the respective pieces of reflected wave data subjected to filter processing, and the vertical axis indicates the signal intensity of the respective pieces of reflected wave data subjected to filter processing. In comparison to the graph of FIG. 6, in the graph of FIG. 7, a difference in signal intensity is small between the two pieces of reflected wave data corresponding to the two adjacent reception scanning lines. Thus, as illustrated in FIG. 9, the ultrasonic image 21 generated from the 40 pieces of reflected wave data subjected to filter processing illustrated in the graph of FIG. 7 becomes an image in which a streak-like artifact is prevented from appearing. The ultrasonic image 21 is an example of an image.

With the ultrasonic diagnostic device 1 according to the first embodiment, a streak-like artifact in the ultrasonic image can be prevented from appearing. Due to this, with the ultrasonic diagnostic device 1 according to the first embodiment, image quality of the ultrasonic image can be prevented from being deteriorated.

Figure 10:
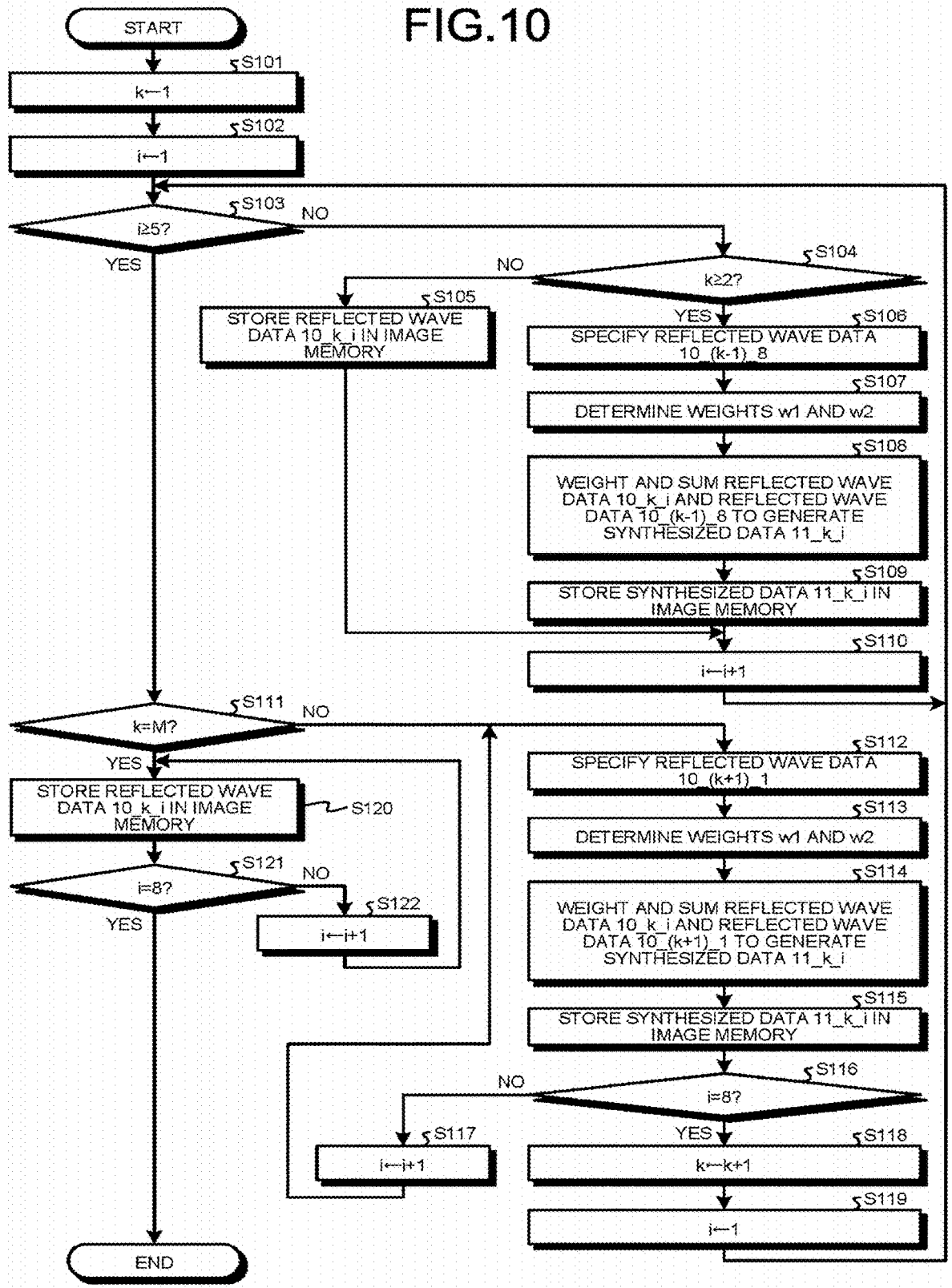
FIG. 10 is a flowchart illustrating an example of a procedure of filter processing performed by the filter processing circuitry according to the first embodiment.

FIG. 10 is a flowchart illustrating an example of a procedure of filter processing performed by the filter processing circuitry 190 according to the first embodiment. The filter processing illustrated in FIG. 10 is, for example, performed by the respective functions 190a to 190c of the filter processing circuitry 190 in a case in which the ultrasonic diagnostic device 1 performs parallel signal processing multiple times to obtain the ultrasonic image data for one frame.

As illustrated in FIG. 10, the specifying function 190a sets "1" as a variable k (Step S101). The specifying function 190a sets "1" as a variable i (Step S102). The specifying function 190a then determines whether a value of the variable i is equal to or larger than 5 (Step S103).

If the value of the variable i is smaller than "5" (No at Step S103), the specifying function 190a determines whether a value of the variable k is equal to or larger than "2" (Step S104). If the value of the variable k is smaller than "2" (No at Step S104), the specifying function 190a stores the reflected wave data 10_k_i in the image memory 160 (Step S105), and advances the process to Step S110.

If the value of the variable k is equal to or larger than "2" (Yes at Step S104), the specifying function 190a specifies reflected wave data 10_(k−1)_8 to be synthesized with the reflected wave data 10_k_i (Step S106).

The weight determining function 190b determines the weight w1 and the weight w2 (Step S107). The weighted sum function 190c then weights and sums the reflected wave data 10_k_i and the reflected wave data 10_(k−1)_8 using the weight w1 and the weight w2 to generate the synthesized data 11_k_i (Step S108). The weighted sum function 190c stores the synthesized data 11_k_i in the image memory 160 (Step S109). The specifying function 190a then increments the value of the variable i by 1 (Step S110), and returns the process to Step S103.

If the value of the variable i is equal to or larger than "5" (Yes at Step S103), the specifying function 190a determines whether the value of the variable k is "M" (Step S111). If the value of the variable k is not "M" (No at Step S111), the specifying function 190a specifies reflected wave data 10_(k+1)_1 to be synthesized with the reflected wave data 10_k_i (Step S112).

The weight determining function 190b determines the weight w1 and the weight w2 (Step S113). The weighted sum function 190c weights and sums the reflected wave data 10_k_i and the reflected wave data 10_(k+1)_1 using the weight w1 and the weight w2 to generate the synthesized data 11_k_i (Step S114). The weighted sum function 190c stores the synthesized data 11_k_1 in the image memory 160 (Step S115). The specifying function 190a determines whether the value of the variable i is "8" (Step S116).

If the value of the variable i is not "8" (No at Step S116), the specifying function 190a increments the value of the variable i by 1 (Step S117), and returns the process to Step S112.

On the other hand, if the value of the variable i is "8" (Yes at Step S116), the specifying function 190a increments the value of the variable k by 1 (Step S118). The specifying function 190a then sets "1" as the variable I (Step S119), and returns the process to Step S103.

If the value of the variable k is "M" (Yes at Step S111), the specifying function 190a stores the reflected wave data 10_k_i in the image memory 160 (Step S120). The specifying function 190a determines whether the value of the variable i is "8" (Step S121). If the value of the variable i is not "8" (No at Step S121), the specifying function 190a increments the value of the variable i by 1 (Step S122), and returns the process to Step S120.

If the value of the variable i is "8" (Yes at Step S121), the specifying function 190a ends the filter processing.

Steps S101 to S106, S110 to S112, and S116 to S122 illustrated in FIG. 10 are steps corresponding to the specifying function 190a. Steps S101 to S106, S110 to S112, and S116 to S122 are steps at which the specifying function 190a is implemented when the filter processing circuitry 190 calls the program corresponding to the specifying function 190a from the storage circuitry 170 to be executed.

Steps S107 and S113 are steps corresponding to the weight determining function 190b. Steps S107 and S113 are steps at which the weight determining function 190b is implemented when the filter processing circuitry 190 calls the program corresponding to the weight determining function 190b from the storage circuitry 170 to be executed.

Steps S108, S109, S114, and S115 are steps corresponding to the weighted sum function 190c. Steps S108, S109, S114, and S115 are steps at which the weighted sum function 190c is implemented when the filter processing circuitry 190 calls the program corresponding to the weighted sum function 190c from the storage circuitry 170 to be executed.

In this case, a total of (8×M) pieces of reflected wave data and synthesized data that are stored in the image memory 160 at Steps S105, S109, S115, and S120 of filter processing are input to the image generation circuitry 150 from the filter processing circuitry 190 via the B-mode processing circuitry 130 or the Doppler processing circuitry 140. The image generation circuitry 150 then generates the ultrasonic image data for one frame based on the total of (8×M) pieces of reflected wave data and synthesized data that have passed through the B-mode processing circuitry 130 or the Doppler processing circuitry 140. That is, the image generation circuitry 150 generates the ultrasonic image data based on a plurality of pieces of reflected wave data subjected to filter processing.

The ultrasonic diagnostic device 1 according to the first embodiment has been described above. With the ultrasonic diagnostic device 1 according to the first embodiment, as described above, image quality of the ultrasonic image can be prevented from being deteriorated.

First Modification and Second Modification of First Embodiment

In the first embodiment described above, described is a case in which the filter processing circuitry 190 performs filter processing on the reflected wave data 10_k_i. However, the filter processing circuitry 190 may similarly perform filter processing on another type of data. Thus, the following describes two modifications in a case in which the filter processing circuitry 190 similarly performs filter processing on another type of data as a first modification and a second modification of the first embodiment.

Figure 11:
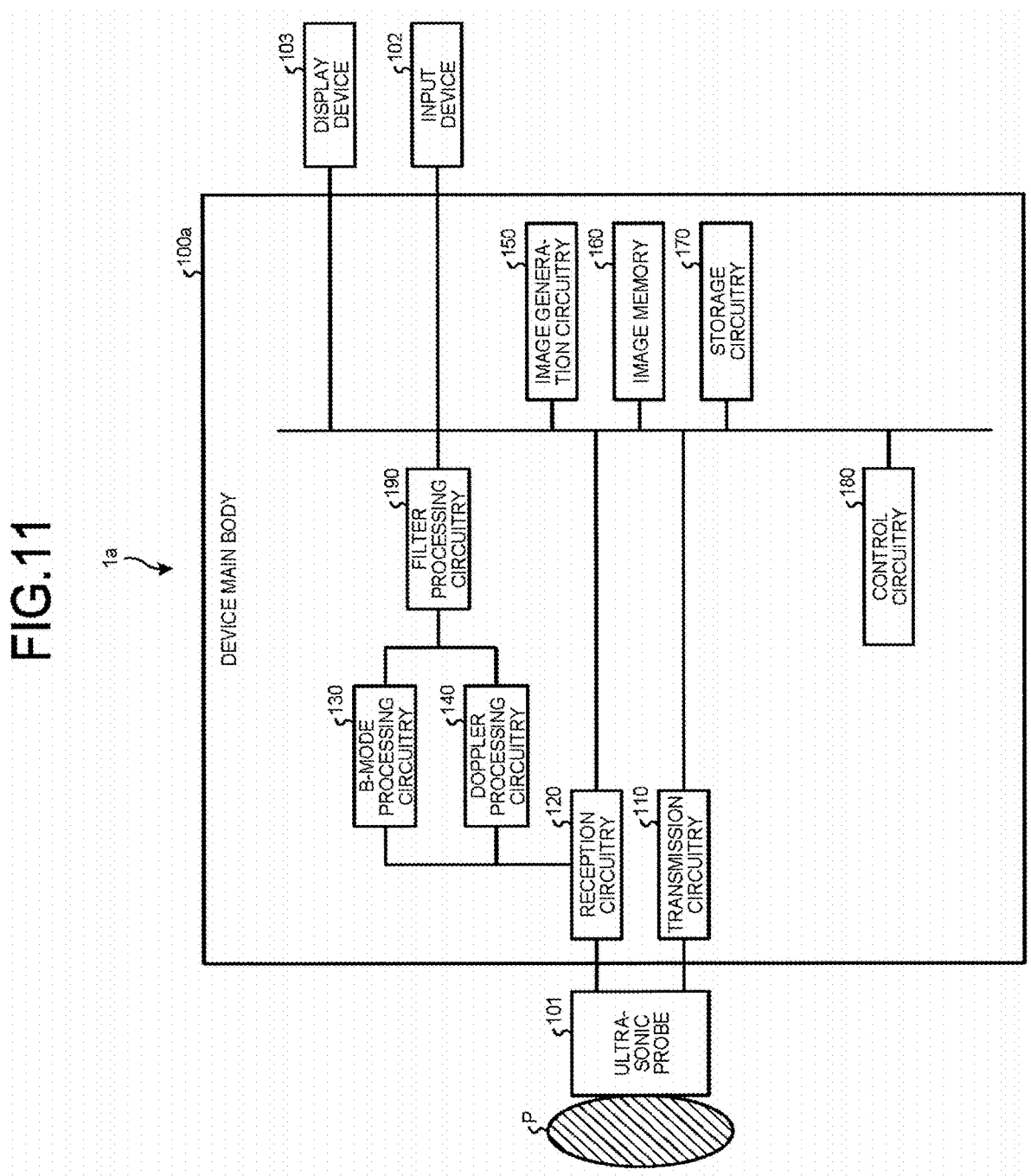
FIG. 11 is a block diagram illustrating a configuration example of an ultrasonic diagnostic device according to a first modification of the first embodiment.

FIG. 11 is a block diagram illustrating a configuration example of an ultrasonic diagnostic device 1a according to the first modification of the first embodiment. The same configuration as that in the first embodiment is denoted by the same reference numeral, and redundant description will not be repeated herein.

As illustrated in FIG. 11, the ultrasonic diagnostic device 1a according to the first modification includes a device main body 100a according to the first modification in place of the device main body 100 according to the first embodiment. In the device main body 100a, the filter processing circuitry 190 is disposed between the image generation circuitry 150, and the B-mode processing circuitry 130 and the Doppler processing circuitry 140.

The filter processing circuitry 190 according to the first modification performs filter processing on the B-mode data output from the B-mode processing circuitry 130 similarly to the first embodiment. The filter processing circuitry 190 also performs filter processing on the Doppler data indicating at least one of a speed value, a power value, and a variance value of the moving object output from the Doppler processing circuitry 140 similarly to the first embodiment. The filter processing circuitry 190 then outputs the B-mode data subjected to filter processing and the Doppler data subjected to filter processing to the image generation circuitry 150. Each of the B-mode data and the Doppler data is an example of a reception signal.

The B-mode data is data obtained by performing logarithmic compression on the reflected wave data that has been subjected to envelope detection processing. Typically, in a case of adding another logarithm to a certain logarithm, two antilogarithms in these logarithms are multiplied together. Thus, in filter processing, weighted sum performed on such data that has been subjected to logarithmic compression is also called weighting multiplication.

FIG. 11 is a block diagram illustrating a configuration example of an ultrasonic diagnostic device 1b according to the second modification of the first embodiment. The same configuration as that in the first embodiment is denoted by the same reference numeral, and redundant description will not be repeated herein.

Figure 12:
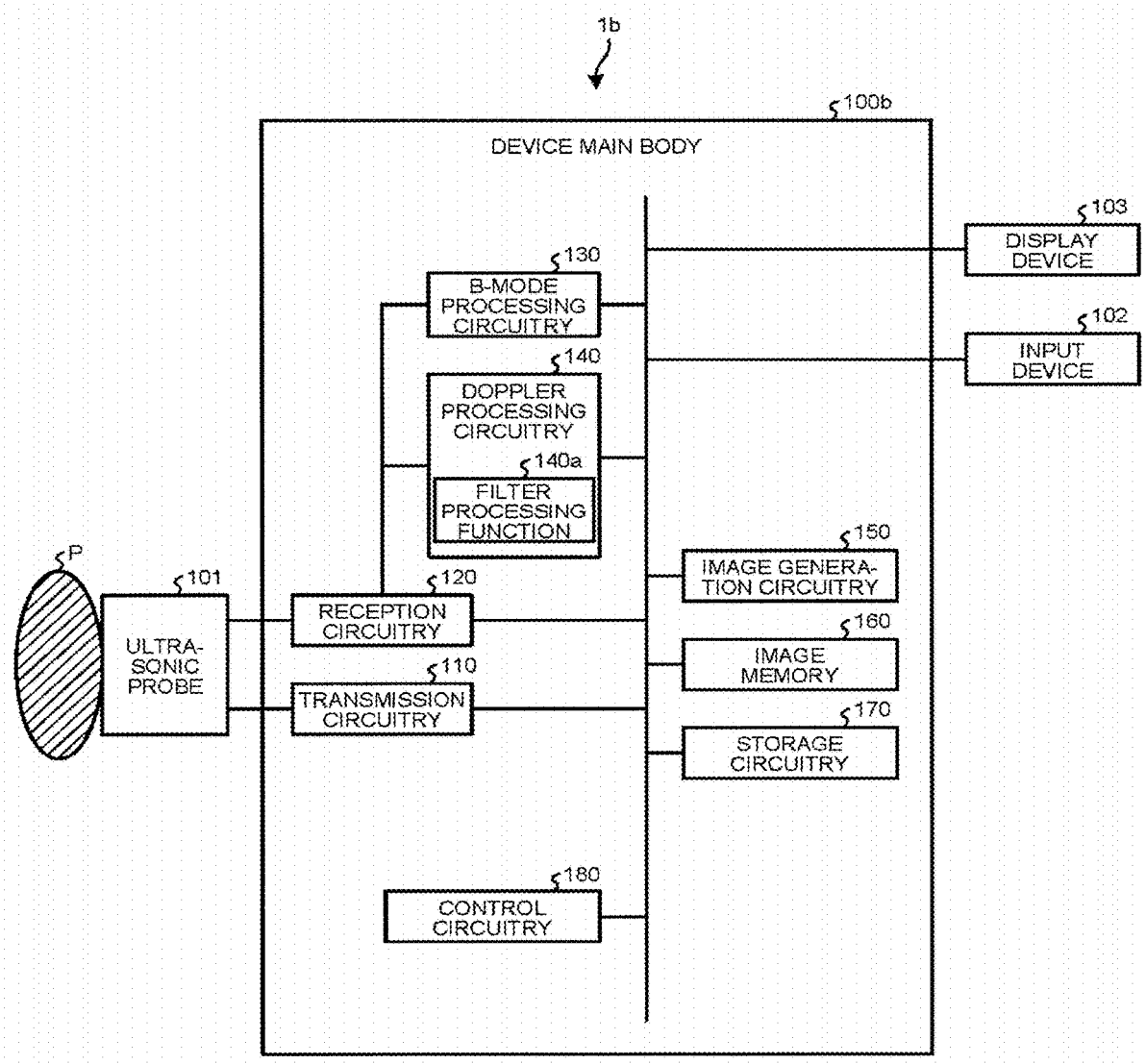
FIG. 12 is a block diagram illustrating a configuration example of an ultrasonic diagnostic device according to a second modification of the first embodiment.

As illustrated in FIG. 12, the ultrasonic diagnostic device 1b according to the second modification includes a device main body 100b according to the second modification in place of the device main body 100 according to the first embodiment. In the device main body 100b, the Doppler processing circuitry 140 has a filter processing function 140a similar to the filter processing function of the filter processing circuitry 190 according to the first embodiment in addition to the function of the Doppler processing circuitry 140 according to the first embodiment. The Doppler processing circuitry 140 reads out a program corresponding to the filter processing function 140a from the storage circuitry 170, and executes the read-out program to implement the filter processing function 140a.

In the second modification, the filter processing function 140a performs filter processing similar to the filter processing according to the first embodiment on the Doppler data indicating at least one of the speed, the power, and the variance of the moving object, or on an autocorrelation value as data subjected to autocorrelation processing (data obtained by performing autocorrelation processing on the reflected wave data). The data obtained by performing autocorrelation processing on the reflected wave data is an example of a reception signal. As in the Doppler processing circuitry 140 described above, the ultrasonic waves are transmitted/received multiple times in the same direction (on the same scanning line), so that the filter processing according to the second modification is preferable in a case in which a time lag caused when the transmission scanning line moves is large, and a phase difference of the reception signal in two times of parallel signal processing with two transmission ultrasonic waves having the adjacent sound fields is relatively larger than a phase difference of the reception signal in one time of parallel signal processing with one transmission ultrasonic wave.

Third Modification of First Embodiment

In the first embodiment, described is a case in which the filter processing circuitry 190 performs filter processing on one piece of reflected wave data as the processing target using one specific piece of reflected wave data. However, the filter processing circuitry 190 may perform filter processing on one piece of reflected wave data as the processing target using a plurality of specific pieces of reflected wave data. Such a modification will be described below as a third modification according to the first embodiment.

Figure 13:
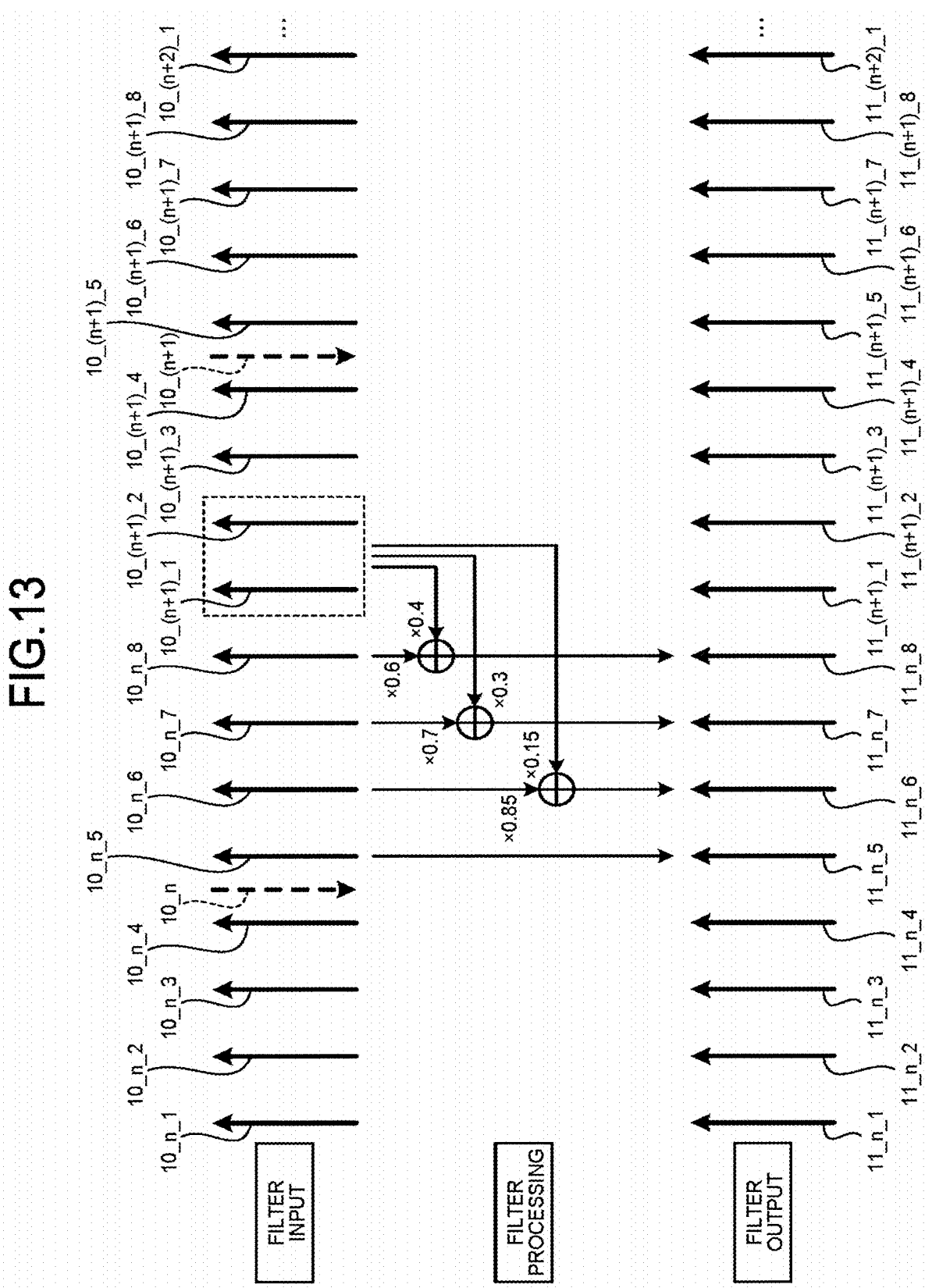

FIG. 13 is a diagram for explaining an example of processing performed by the filter processing circuitry 190 according to the third modification of the first embodiment. The same configuration as that in the first embodiment is denoted by the same reference numeral, and redundant description will not be repeated herein.

As illustrated in FIG. 13, similarly to the first embodiment, the specifying function 190a specifies the reception scanning line 50_(n+1)_1 closest to the reception scanning line 50_n_8 (not illustrated) corresponding to the reflected wave data 10_n_8 in arrangement order of the reception scanning lines. Similarly to the first embodiment, the specifying function 190a specifies the reflected wave data 10_(n+1)_1 corresponding to the reception scanning line 50_(n+1)_1.

In the third modification, the specifying function 190a further specifies a reception scanning line 50_(n+1)_2 next closest to the reception scanning line 50_n_8 in arrangement order of the reception scanning lines. The specifying function 90a then specifies the reflected wave data 10_(n+1)_2 corresponding to the reception scanning line 50_(n+1)_2.

Similarly, the specifying function 100a specifies two pieces of reflected wave data 10_(n+1)_1 and 10_(n+1)_2 as pieces of reflected wave data to be synthesized with the respective pieces of reflected wave data 10_n_5 to 10_n_7.

The weighted sum function 190c performs filter processing on the respective pieces of reflected wave data 10_n_5 to 10_n_8 using two specific pieces of reflected wave data 10_(n+1)_1 and 10_(n+1)_2.

For example, the weighted sum function 190c weights and sums the two specific pieces of reflected wave data 10_(n+1)_1 and 10_(n+1)_2 to generate one specific piece of reflected wave data (synthesized reflected wave data). The weighted sum function 190c then performs filter processing on each of the pieces of reflected wave data 10_n_5 to 10_n_8 using one specific piece of synthesized reflected wave data.

Fourth Modification of First Embodiment

The first embodiment describes a case in which, assuming that j is an integral number equal to or larger than 1 and equal to or smaller than (M−1), the sound field of the transmission ultrasonic wave at the j-th time and the sound field of the transmission ultrasonic wave at the (j+1)-th time are adjacent to each other. The first embodiment also describes a case in which intervals between the reception scanning lines are regular intervals. However, the sound field of the transmission ultrasonic wave at the j-th time may be partially overlapped with the sound field of the transmission ultrasonic wave at the (j+1)-th time. In addition, the intervals between the reception scanning lines are not necessarily regular intervals. The following describes such a modification as a fourth modification of the first embodiment.

Figure 14:
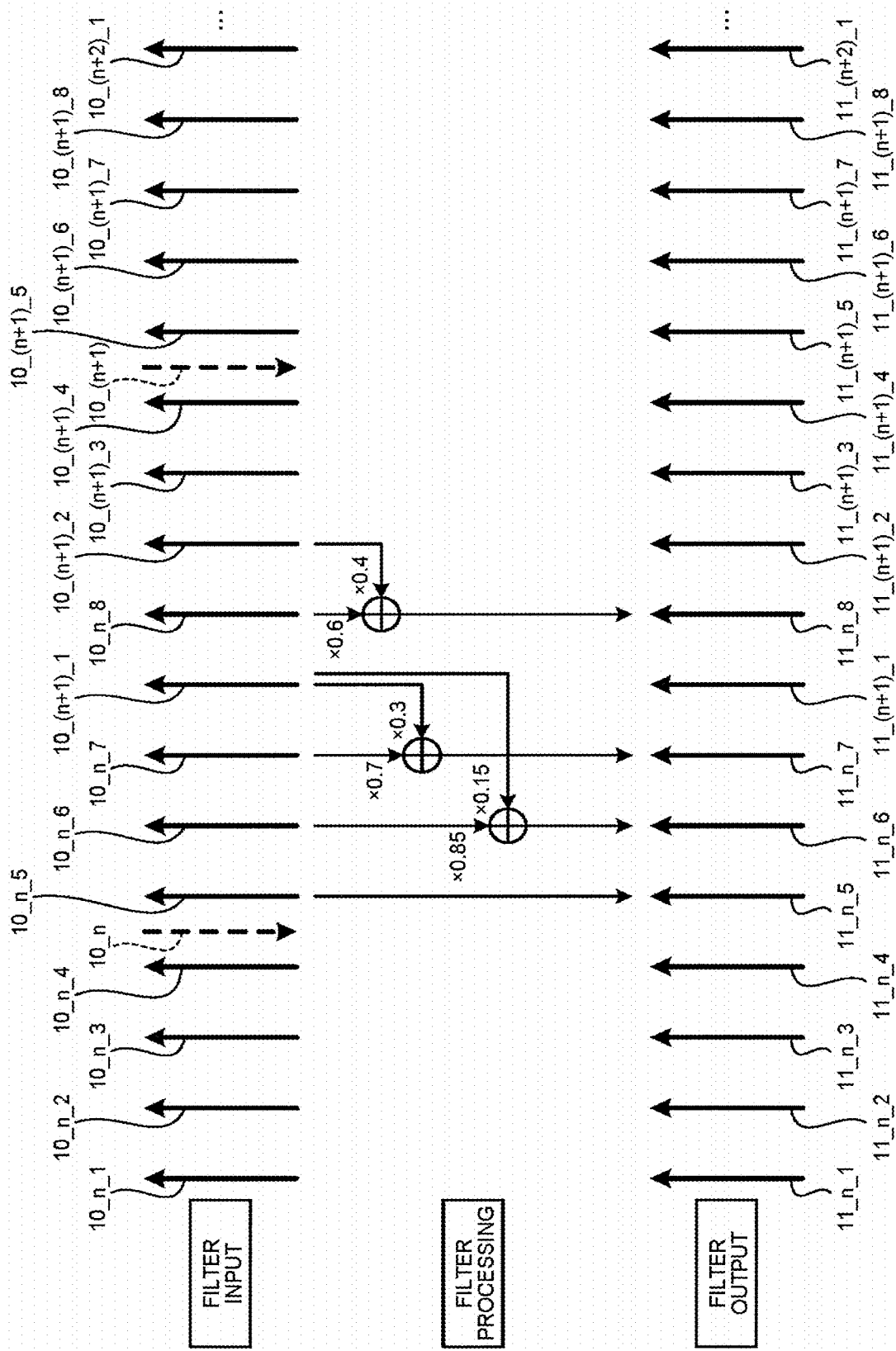
FIG. 14 is a diagram for explaining an example of processing performed by filter processing circuitry according to a fourth modification of the first embodiment.

FIG. 14 is a diagram for explaining an example of processing performed by the filter processing circuitry 190 according to the fourth modification of the first embodiment. The same configuration as that in the first embodiment is denoted by the same reference numeral, and redundant description will not be repeated herein.

As illustrated in FIG. 14, the interval between the reception scanning line 50_n_7 (not illustrated) corresponding to the reflected wave data 10_n_7 and the reception scanning line 50_n_8 (not illustrated) corresponding to the reflected wave data 10_n_8 is larger than the interval between the reception scanning line 50_n_7 and the reception scanning line 50_n_8 according to the first embodiment.

Similarly, the interval between the reception scanning line 50_(n+1)_1 (not illustrated) corresponding to the reflected wave data 10_(n+1)_1 illustrated in FIG. 14 and the reception scanning line 50_(n+1)_2 (not illustrated) corresponding to the reflected wave data 10_(n+1)_2 is larger than the interval between the reception scanning line 50_(n+1)_1 and the reception scanning line 50_(n+1)_2 according to the first embodiment.

As a result, part of the sound field of the transmission ultrasonic wave 10_n at the n-th time illustrated in FIG. 14 is overlapped with part of the sound field of the transmission ultrasonic wave 10_(n+1) at the (n+1)-th time. A plurality of reception scanning lines 50_n_1 to 50_n_8 (not illustrated) and a plurality of reception scanning lines 50_(n+1)_1 to 50_(n+1)_8 (not illustrated) are set at different positions by the reception circuitry 120.

Also in a case as illustrated in FIG. 14, similarly to the first embodiment, the filter processing circuitry 190 according to the fourth modification performs filter processing on the reflected wave data as the processing target. For example, as illustrated in FIG. 14, the specifying function 190a specifies the reflected wave data 10_(n+1)_2 as the reflected wave data to be synthesized with the reflected wave data 10_n_8. The specifying function. 190a specifies the reflected wave data 10_(n+1)_1 as the reflected wave data to be synthesized with the pieces of reflected wave data 10_n_5 to 10_n_7.

The weight determining function 190b then determines the weight w1 for the reflected wave data 10_n_8 to be "0.6", and determines the weight w2 for the reflected wave data 10_(n+1)_2 to be "0.4". The weight determining function 190b determines the weight w1 for the reflected wave data 10_n_7 to be "0.7", and determines the weight w2 for the reflected wave data 10_(n+1)_1 to be "0.3". The weight determining function 190b determines the weight w1 for the reflected wave data 10_n_6 to be "0.85", and determines the weight w2 for the reflected wave data 10_(n+1)_1 to be "0.15". The weight determining function 190b determines the weight w1 for the reflected wave data 10_n_5 to be "1.0", and determines the weight w2 for the reflected wave data 10_(n+1)_1 to be "0".

The weighted sum function 190c synthesizes (sums) data obtained by multiplying the reflected wave data 10_n_8 by the weight "0.6" and data obtained by multiplying the reflected wave data 10_(n+1)_2 by the weight "0.4" to generate the synthesized data 11_n_8.

The weighted sum function 190c also synthesizes data obtained by multiplying the reflected wave data 10_n_7 by the weight "0.7" and data obtained by multiplying the reflected wave data 10_(n+1)_1 by the weight "0.3" to generate the synthesized data 11_n_7. The weighted sum function 190c also synthesizes data obtained by multiplying the reflected wave data 10_n_6 by the weight "0.85" and data obtained by multiplying the reflected wave data 10_(n+1)_1 by the weight "0.15" to generate the synthesized data 11_n_6.

The weighted sum function 190c also synthesizes data obtained by multiplying the reflected wave data 10_n_5 by the weight "1.0" and data obtained by multiplying the reflected wave data 10_(n+1)_1 by the weight "0" to generate the synthesized data 11_n_5.

In this way, the weighted sum function 190c performs weighted sum processing of weighting and summing each of the pieces of reflected wave data 10_n_5 to 10_n_8 and the specific reflected wave data 10_(n+1)_1 or the specific reflected wave data 10_(n+1)_2. The pieces of reflected wave data 10_n_5 to 10_n_8 are pieces of data corresponding to the reception scanning lines 50_n_5 to 50_n_8 (not illustrated) set at a portion larger than part the sound field of the ultrasonic wave 10_n overlapped with part of the sound field of the ultrasonic wave 10_(n+1). The specific reflected wave data 10_(n+1)_1 is data corresponding to the pieces of reflected wave data 10_n_5 to 10_n_7. The specific reflected wave data 10_(n+1)_2 is data corresponding to the reflected wave data 10_n_8.

According to the fourth modification, filter processing can be performed even when the sound fields of the two transmission ultrasonic waves are partially overlapped with each other and the intervals between the reception scanning lines are not regular intervals.

Fifth Modification and Sixth Modification of First Embodiment

In the first embodiment described above, described is a case in which the filter processing circuitry 190 determines the weights w1 and w2 based on the arrangement order of the reception scanning lines for each piece of the reflected wave data as the processing target. However, the filter processing circuitry 190 may determine the weights w1 and w2 based on information other than the arrangement order of the reception scanning lines. The following describes two modifications for determining the weights w1 and w2 based on information other than the arrangement order of the reception scanning lines as a fifth modification and a sixth modification of the first embodiment.

Figure 15:
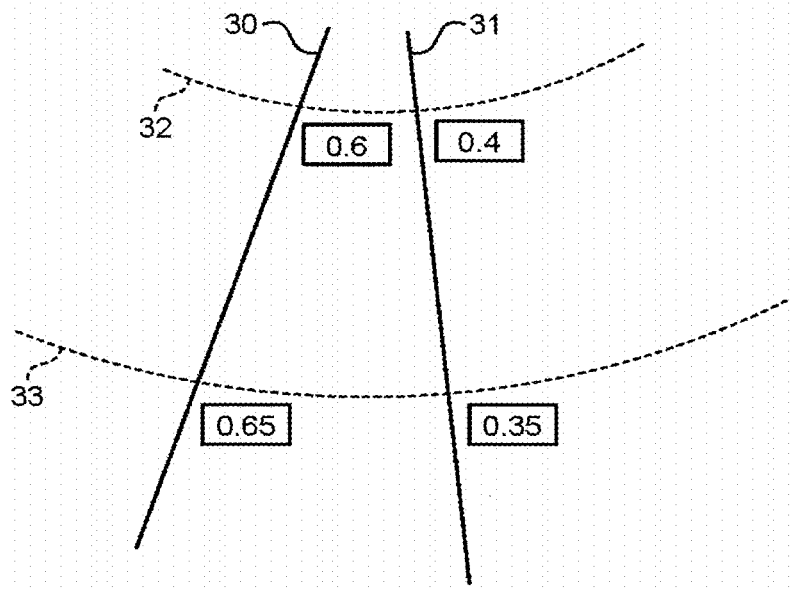
FIG. 15 is a diagram for explaining an example of processing performed by filter processing circuitry according to a third modification of the first embodiment.

FIG. 15 is a diagram for explaining an example of processing performed by the filter processing circuitry 190 according to the fifth modification of the first embodiment. FIG. 15 illustrates a reception scanning line 30 corresponding to the reflected wave data as the processing target and a reception scanning line 31 corresponding to the specific reflected wave data to be synthesized with the reflected wave data as the processing target. In a case in which the ultrasonic probe 101 is a convex ultrasonic probe or a sector ultrasonic probe, a distance (interval) between the reception scanning line 30 and the reception scanning line 31 in real space is increased as a depth (observing position) is deeper. For example, as illustrated in FIG. 15, the distance between the reception scanning line 30 and the reception scanning line 31 in real space is longer at a depth 33 than at a depth 32. In a case in which the ultrasonic probe 101 is a linear ultrasonic probe, the distance (interval) between the reception scanning lines in real space varies in accordance with the number of scanning lines set in the same scanning range.

Thus, the weight determining function 190b according to the fifth modification determines the weights w1 and w2 for each of the pieces of reflected wave data as the processing target based on the distance between the reception scanning line 30 corresponding to the reflected wave data as the processing target and the reception scanning line 31 corresponding to the specific reflected wave data in real space. Specifically, the weight determining function 190b determines the eights w1 and w2 so that the weight w1 increases as the distance becomes longer.

For example, as illustrated in FIG. 15, at the depth 32, the weight determining function 190b determines the weight w1 for the reflected wave data as the processing target to be "0.6", and determines the weight w2 for the specific reflected wave data to be "0.4". At the depth 33 deeper than the depth 32, the weight determining function 190b determines the weight w1 for the reflected wave data as the processing target to be "0.65", and determines the weight w2 for the specific reflected wave data to be "0.35" because the distance in real space varies.

According to the fifth modification, the distance in real space is taken into consideration in determining the weights w1 and w2, so that the weights w1 and w2 can be determined more accurately. As a result, image quality of the ultrasonic image can be further prevented from being deteriorated.

Figure 16:
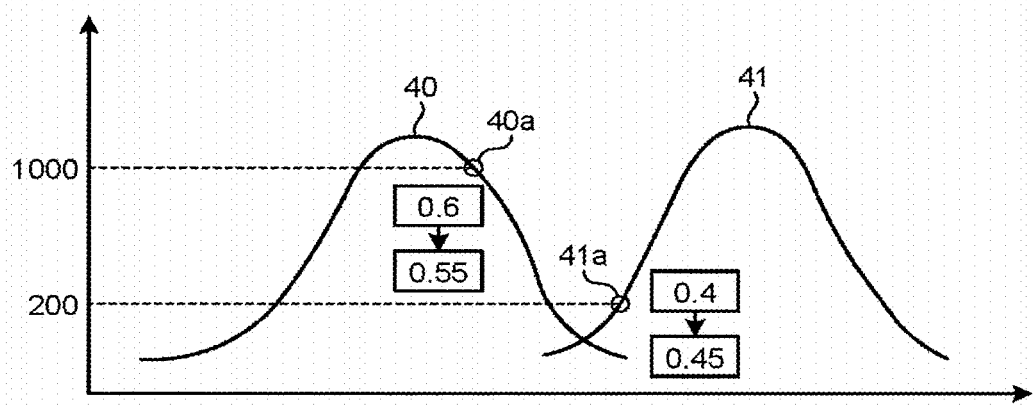
FIG. 16 is a diagram for explaining an example of processing performed by filter processing circuitry according to a sixth modification of the first embodiment.

FIG. 16 is a diagram for explaining an example of processing performed by the filter processing circuitry 190 according to the sixth modification of the first embodiment. FIG. 16 illustrates a receiving position 40a of the reflected wave data as the processing target and corresponding transmission sensitivity distribution 40, and a receiving position 41a of the specific reflected wave data to be synthesized with the reflected wave data as the processing target and corresponding transmission sensitivity distribution 41. In this case, the receiving position of the reflected wave data indicates a position of the reception scanning line corresponding to the reflected wave data generated by the reception circuitry 120. The transmission sensitivity distribution indicates distribution of transmission sensitivity based on a transmission sound field of the ultrasonic wave that is generated based on the drive signal supplied from the transmission circuitry 110 in obtaining the reflected wave data. Generally, the transmission sensitivity can be obtained based on the transmission sound field, reception sensitivity can be obtained based on a reception sound field, and transmission/reception sensitivity can be obtained by performing convolution thereon. However, for simplification, the reception sound field herein is assumed to be constant irrespective of the receiving position, and the transmission/reception sensitivity is assumed to vary in accordance with the transmission sensitivity distribution and the receiving position.

The horizontal axis illustrated in FIG. 16 indicates a position of each of the reception scanning lines in an azimuth direction, and the vertical axis indicates the transmission/reception sensitivity. FIG. 16 illustrates a case in which the transmission/reception sensitivity of the reflected wave data as the processing target (reflected wave data corresponding to the receiving position 40a) is "1000", and the transmission/reception sensitivity of the specific reflected wave data to be synthesized with the reflected wave data as the processing target (reflected wave data corresponding to the receiving position 41a) is "200".

In the sixth modification, the weight determining function 190b increases the weight for the reflected wave data the transmission/reception sensitivity of which is relatively lower to prevent a streak-like artifact from appearing. For example, in a case illustrated in FIG. 16, the weight determining function 190b modifies, as follows, the weights w1 (0.6) and w2 (0.4) that are determined based on arrangement order of the transmission/reception scanning lines. For example, to prevent a streak-like artifact from appearing, the weight determining function 190b increases the weight w2 from "0.4" to "0.45", the w2 for the specific reflected wave data as the reflected wave data the transmission/reception sensitivity of which is relatively lower. At the same time, the weight determining function 190b reduces the weight w1 from "0.6" to "0.55".

In this way, the weight determining function 190b according to the sixth modification determines the weights w1 and w2 used for weighted sum processing for each of the pieces of reflected wave data as the processing target based on the transmission/reception sensitivity of the reflected wave data as the processing target and the transmission/reception sensitivity of the specific reflected wave data.

Thus, according to the sixth modification, the transmission/reception sensitivity is taken into consideration in determining the weights w1 and w2, so that the weights w1 and w2 can be determined more accurately. As a result, image quality of the ultrasonic image can be further prevented from being deteriorated.

second Embodiment

Next, the following describes a second embodiment. FIG. 17 is a diagram for illustrating a configuration example of a medical image processing device 300 according to the second embodiment. As illustrated in FIG. 17, the medical image processing device 300 is connected to an ultrasonic diagnostic device 200 and an image storage device 400 via a network 500. The configuration illustrated in FIG. 17 is merely an example, and various devices such as a terminal device may be connected to the network 500 in addition to the ultrasonic diagnostic device 200, the image storage device 400, and the medical image processing device 300 illustrated in the drawing.

Similarly to the ultrasonic diagnostic device 1 according to the first embodiment, the ultrasonic diagnostic device 200 performs parallel signal processing multiple times to obtain the ultrasonic image data for one frame. The ultrasonic diagnostic device 200 then transmits, to the image storage device 400 and the medical image processing device 300, a plurality of pieces of reflected wave data obtained by performing parallel signal processing multiple times.

The image storage device 400 stores the pieces of reflected wave data collected by the ultrasonic diagnostic device 200. For example, the image storage device 400 is implemented by a computer appliance such as a server device. The image storage device 400 acquires a plurality of pieces of reflected wave data from the ultrasonic diagnostic device 200 via the network 500, and stores the acquired pieces of reflected wave data in a memory such as a hard disk or an optical disc that is disposed inside the device or outside the device. The image storage device 400 transmits the reflected wave data stored in the memory to the medical image processing device 300 in response to a request from the medical image processing device 300.

The medical image processing device 300 acquires the pieces of reflected wave data from the ultrasonic diagnostic device 200 and the image storage device 400 via the network 500, and processes the acquired pieces of reflected wave data. For example, the medical image processing device 300 acquires the pieces of reflected wave data from the ultrasonic diagnostic device 200 or the image storage device 400, stores the acquired pieces of reflected wave data in a memory 320 (described later), and performs various kinds of processing on the pieces of reflected wave data stored in the memory 320. The medical image processing device 300 then causes a display device 340 (described later) to display an image after the processing (for example, an ultrasonic image for display) and the like.

As illustrated in FIG. 1, the medical image processing device 300 includes a communication interface 310, the memory 320, an input device 330, the display device 340, and processing circuitry 350.

The communication interface 310 is connected to the processing circuitry 350, and controls transmission of various kinds of data between the ultrasonic diagnostic device 200 and the image storage device 400 that are connected via the network 500, and communication between the ultrasonic diagnostic device 200 and the image storage device 400. For example, the communication interface 310 is implemented by a network card, a network adapter, and a network interface controller (NIC). For example, the communication interface 310 receives a plurality of pieces of reflected wave data from the ultrasonic diagnostic device 200 or the image storage device 400, and outputs the received pieces of reflected wave data to the processing circuitry 350.

The memory 320 is connected to the processing circuitry 350, and stores various kinds of data. For example, the memory 320 is implemented by a semiconductor memory element such as a RAM and a flash memory, a hard disk, or an optical disc. In the present embodiment, the memory 320 stores the pieces of reflected wave data received from the ultrasonic diagnostic device 200 or the image storage device 400. Specifically, the memory 320 stores the pieces of reflected wave data obtained for each time of transmission/reception of the ultrasonic waves performed by the ultrasonic probe 101 corresponding to the number of times of transmission/reception of the ultrasonic waves. For example, the memory 320 stores the pieces of reflected wave data obtained through M times of parallel signal processing.

The memory 320 also stores various kinds of information used for processing of the processing circuitry 350, a processing result obtained by the processing circuitry 350, and the like. For example, the memory 320 stores image data for display and the like generated by the processing circuitry 350.

The input device 330 is connected to the processing circuitry 350, and converts an input operation received from the operator into an electric signal to be output to the processing circuitry 350. For example, the input device 330 is implemented by a trackball, a switch button, a mouse, and a keyboard for performing various kinds of setting, a touch pad having an operation surface touched by a user to perform an input operation, a touch screen integrating a display screen and a touch pad, a non-contact input device using an optical sensor, or a voice input device.

The display device 340 is connected to the processing circuitry 350, and displays various kinds of information and various images output from the processing circuitry 350. For example, the display device 340 is implemented by a liquid crystal monitor, a CRT monitor, and the like. For example, the display device 340 displays a GUI for receiving an instruction from the operator, various images for display, and various processing results obtained by the processing circuitry 350. The display device 340 is an example of a display unit.

The processing circuitry 350 controls respective components included in the medical image processing device 300 in accordance with an input operation received from the operator via the input device 330. For example, the processing circuitry 350 is implemented by a processor. In the present embodiment, the processing circuitry 350 stores a plurality of pieces of reflected wave data output from the communication interface 310 in the memory 320 corresponding to the number of times of transmission/reception of the ultrasonic waves. The processing circuitry 350 also controls the display device 340 to display an ultrasonic image for display indicated by ultrasonic image data for display that is generated by an image generating function 353.

As illustrated in FIG. 17, the processing circuitry 350 includes a filter processing function 351, a signal processing function 352, and the image generating function 353. In this case, for example, each of the processing functions including the filter processing function 351, the signal processing function 352, and the image generating function 353 as components of the processing circuitry 350 illustrated in FIG. 17 is stored in the memory 320 as a computer-executable program. The processing circuitry 350 reads out each program from the memory 320, and executes the read-out program to implement a function corresponding to the program. In other words, the processing circuitry 350 that has read out the programs has the respective functions illustrated in the processing circuitry 350 in FIG. 17.

Alternatively, all processing functions including the filter processing function 351, the signal processing function 352, and the image generating function 353 may be stored in the memory 320 as one computer-executable program. For example, such a program is also called a medical image processing program. In this case, the processing circuitry 350 reads out the medical image processing program from the memory 320, and executes the read-out medical image processing program to implement the filter processing function 351, the signal processing function 352, and the image generating function 353 corresponding to the medical image processing program.

The filter processing function 351 corresponds to the specifying function 190a, the weight determining function 190b, and the weighted sum function 190c of the filter processing circuitry 190 illustrated in FIG. 3. The filter processing function 351 performs processing similarly to the filter processing circuitry 190 according to the first embodiment using the reflected wave data stored in the memory 320. The filter processing function 351 is an example of a filter processing unit.

The signal processing function 352 has a function similar to the function of the B-mode processing circuitry 130 and the function of the Doppler processing circuitry 140 illustrated in FIG. 1. For example, the signal processing function 352 performs processing, similarly to the B-mode processing circuitry 130 and the Doppler processing circuitry 140, on the reflected wave data on which filter processing is performed by the filter processing function 351.

The image generating function 353 has a function similar to the function of the image generation circuitry 150 illustrated in FIG. 1. For example, the image generating function 353 generates an ultrasonic image data for display from the data output from the signal processing function 352. The image generating function 353 is an example of a generation unit.

The medical image processing device 300 according to the second embodiment has been described above. With the medical image processing device 300 according to the second embodiment, image quality of the ultrasonic image can be prevented from being deteriorated similarly to the ultrasonic diagnostic device 1 according to the first embodiment.

According to at least one of the embodiments and the modifications described above, image quality of the ultrasonic image can be prevented from being deteriorated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic device, comprising:
reception circuitry configured to output a plurality of reception signals corresponding to a plurality of reception scanning lines for each time of transmission/reception of ultrasonic waves performed by an ultrasonic probe, the plurality of reception signals including (1) a first group of plural reception signals received in response to a first ultrasonic wave transmitted from the ultrasonic probe, and (2) a second group of plural reception signals received in response to a second ultrasonic wave transmitted from the ultrasonic probe, wherein a first sound field of the first ultrasonic wave is adjacent to or partially overlapped with a second sound field of the second ultrasonic wave; and
processing circuitry configured to
perform filter processing on each of plural first reception signals of the first group of plural reception signals using a synthesized signal obtained by synthesizing plural second reception signals among the second group of plural reception signals to produce at least one filtered reception signal, the at least one filtered reception signal corresponding to at least one reception scanning line among plural first reception scanning lines corresponding to the plural first reception signals, and
generate image data based on the at least one filtered reception signal,
wherein the plural first reception scanning lines corresponding to the plural first reception signals are set at positions different from positions at which reception scanning lines corresponding to the plural second reception signals are set;
wherein, when the first sound field overlaps the second sound field, the processing circuitry is further configured to perform, as the filter processing, weighted sum processing of weighting and summing each of plural first reception signals and the synthesized signal, wherein the plural first reception signals correspond to the plural first reception scanning lines, which are set at a portion of the first sound field that is overlapped with the second sound field; and
wherein the processing circuitry is further configured to determine a respective weight used for the weighted sum processing for each of the plural first reception signals based on an arrangement order of the plural first reception scanning lines corresponding to the plural first reception signals and a reception scanning line corresponding to the synthesized signal, or based on a distance between each of the plural first reception scanning lines corresponding to each of the plural first reception signals and the reception scanning line corresponding to the synthesized signal.

2. The ultrasonic diagnostic device according to claim 1, wherein the reception scanning line corresponding to the synthesized signal is a scanning line closest to the plural first reception scanning lines corresponding to the plural first reception signals.

3. The ultrasonic diagnostic device according to claim 1, wherein the processing circuitry is further configured to determine a weight used for the weighted sum processing for each of the plural first reception signals based on transmission/reception sensitivity of the each of the plural first reception signals and transmission/reception sensitivity of the synthesized signal.

4. The ultrasonic diagnostic device according to claim 1, wherein the processing circuitry is further configured to perform the filter processing on data including phase information, B-mode data, and Doppler data indicating at least one of a speed value, a power value, and a variance value of a moving object.

5. A medical image processing device, comprising:
storage circuitry configured to store a plurality of reception signals obtained for each time of transmission/reception of ultrasonic waves performed by an ultrasonic probe corresponding to a number of times of transmission/reception of ultrasonic waves, the plurality of reception signals including (1) a first group of plural reception signals received in response to a first ultrasonic wave transmitted from the ultrasonic probe and (2) a second group of plural reception signals received in response to a second ultrasonic wave transmitted from the ultrasonic probe, wherein a first sound field of the first ultrasonic wave is adjacent to or partially overlapped with a second sound field of the second ultrasonic wave; and
processing circuitry configured to
refer to storage content of the storage circuitry and perform filter processing on each of plural first reception signals of the first group of plural reception signals using a synthesized signal obtained by synthesizing plural second reception signals among the second group of plural reception signals to produce at least one filtered reception signal, the at least one filtered reception signal corresponding to at least one reception scanning line among plural first reception scanning lines corresponding to the plural first reception signals, and
generate image data based on the at least one filtered reception signal,
wherein the plural first reception scanning lines corresponding to the plural first reception signals are set at positions different from positions at which reception scanning lines corresponding to the plural second reception is signals are set;
wherein, when the first sound field overlaps the second sound field, the processing circuitry is further configured to perform, as the filter processing, weighted sum processing of weighting and summing each of plural first reception signals and the synthesized signal, wherein the plural first reception signals correspond to the plural first reception scanning lines, which are set at a portion of the first sound field that is overlapped with the second sound field; and
wherein the processing circuitry is further configured to determine a respective weight used for the weighted sum processing for each of the plural first reception signals based on an arrangement order of the plural first reception scanning lines corresponding to the plural first reception signals and a reception scanning line corresponding to the synthesized signal, or based on a distance between each of the plural first reception scanning lines corresponding to each of the plural first reception signals and the reception scanning line corresponding to the synthesized signal.

6. A medical image processing method executed by a computer, the method comprising:
referring to storage content of storage circuitry configured to store a plurality of reception signals obtained for each time of transmission/reception of ultrasonic waves performed by an ultrasonic probe corresponding to a number of times of transmission/reception of the ultrasonic waves, the plurality of reception signals including (1) a first group of plural reception signals received in response to a first ultrasonic wave transmitted from the ultrasonic probe and (2) a second group of plural reception signals received in response to a second ultrasonic wave transmitted from the ultrasonic probe, wherein a first sound field of the first ultrasonic wave is adjacent to or partially overlapped with a second sound field of the second ultrasonic wave,
performing filter processing on each of plural first reception signals of the first group of plural reception signals using a synthesized signal obtained by synthesizing plural second reception signals among the second group of plural reception signals to produce at least one filtered reception signal, the at least one filtered reception signal corresponding to at least one reception scanning line among plural first reception scanning lines corresponding to the plural first reception signals, and
generating image data based on the at least one filtered reception signal,
wherein the plural first reception scanning lines corresponding to the plural first reception signals are set at positions different from positions at which reception scanning lines corresponding to the plural second reception signals are set;
wherein, when the first sound field overlaps the second sound field, the performing the filter processing comprises performing, as the filter processing, weighted sum processing by weighting and summing each of the plural first reception signals and the synthesized signal, wherein the plural first reception signals correspond to the plural first reception scanning lines, which are set at a portion of the first sound field that is overlapped with the second sound field; and
wherein the performing the filter processing comprises determining a respective weight used for the weighted sum processing for each of the plural first reception signals based on an arrangement order of the plural first reception scanning lines corresponding to the plural first reception signals and a reception scanning line corresponding to the synthesized signal, or based on a distance between each of the plural first reception scanning lines corresponding to each of the plural first reception signals and the reception scanning line corresponding to the synthesized signal.

7. The medical image processing device according to claim 5, wherein the reception scanning line corresponding to the synthesized signal is a scanning line closest to the plural first reception scanning lines corresponding to the plural first reception signals.

8. The medical image processing method according to claim 6, wherein the reception scanning line corresponding to the synthesized signal is a scanning line closest to the plural first reception scanning lines corresponding to the plural first reception signals.

9. The ultrasonic diagnostic device according to claim 1, wherein first and second ultrasonic waves are transmitted in a same direction.

10. The ultrasonic diagnostic device according to claim 1, wherein the processing circuitry is further configured to perform the filter processing by performing autocorrelation processing on phase information, as the first and second groups of plural receptions signals.

11. An ultrasonic diagnostic device, comprising:
reception circuitry configured to output a plurality of reception signals corresponding to a plurality of reception scanning lines for each time of transmission/reception of ultrasonic waves performed by an ultrasonic probe, the plurality of reception signals including (1) a first group of plural reception signals received in response to a first ultrasonic wave transmitted from the ultrasonic probe, and (2) a second group of plural reception signals received in response to a second ultrasonic wave transmitted from the ultrasonic probe, wherein a first sound field of the first ultrasonic wave is adjacent to or partially overlapped with a second sound field of the second ultrasonic wave; and
processing circuitry configured to
perform filter processing on each of plural first reception signals of the first group of plural reception signals using a synthesized signal obtained by synthesizing plural second reception signals among the second group of plural reception signals to produce at least one filtered reception signal, the at least one filtered reception signal corresponding to at least one reception scanning line among plural first reception scanning lines corresponding to the plural first reception signals, and
generate image data based on the at least one filtered reception signal,
wherein the plural first reception scanning lines corresponding to the plural first reception signals are set at positions different from positions at which reception scanning lines corresponding to the plural second reception signals are set, wherein the processing circuitry is further configured to perform, as the filter processing, weighted sum processing of weighting and summing each of the plural first reception signals and the synthesized signal; and
wherein the processing circuitry is further configured to determine a respective weight used for the weighted sum processing for each of the plural first reception signals based on an arrangement order of the plural first reception scanning lines corresponding to the plural first reception signals and a reception scanning line corresponding to the synthesized signal, or based on a distance between each of the plural first reception scanning lines corresponding to each of the plural first reception signals and the reception scanning line corresponding to the synthesized signal.

12. A medical image processing device, comprising:
storage circuitry configured to store a plurality of reception signals obtained for each time of transmission/reception of ultrasonic waves performed by an ultrasonic probe corresponding to a number of times of transmission/reception of ultrasonic waves, the plurality of reception signals including (1) a first group of plural reception signals received in response to a first ultrasonic wave transmitted from the ultrasonic probe and (2) a second group of plural reception signals received in response to a second ultrasonic wave transmitted from the ultrasonic probe, wherein a first sound field of the first ultrasonic wave is adjacent to or partially overlapped with a second sound field of the second ultrasonic wave; and
processing circuitry configured to
refer to storage content of the storage circuitry and perform filter processing on each of plural first reception signals of the first group of plural reception signals using a synthesized signal obtained by synthesizing plural second reception signals among the second group of plural reception signals to produce at least one filtered reception signal, the at least one filtered reception signal corresponding to at least one reception scanning line among plural first reception scanning lines corresponding to the plural first reception signals, and
generate image data based on the at least one filtered reception signal,
wherein the plural first reception scanning lines corresponding to the plural first reception signals are set at positions different from positions at which reception scanning lines corresponding to the plural second reception signals are set, wherein the processing circuitry is further configured to perform, as the filter processing, weighted sum processing of weighting and summing each of the plural first reception signals and the synthesized signal; and
wherein the processing circuitry is further configured to determine a respective weight used for the weighted sum processing for each of the plural first reception signals based on an arrangement order of the plural first reception scanning lines corresponding to the plural first reception signals and a reception scanning line corresponding to the synthesized signal, or based on a distance between each of the plural first reception scanning lines corresponding to each of the plural first reception signals and the reception scanning line corresponding to the synthesized signal.

13. A medical image processing method executed by a computer, the method comprising:
referring to storage content of storage circuitry configured to store a plurality of reception signals obtained for each time of transmission/reception of ultrasonic waves performed by an ultrasonic probe corresponding to a number of times of transmission/reception of the ultrasonic waves, the plurality of reception signals including (1) a first group of plural reception signals received in response to a first ultrasonic wave transmitted from the ultrasonic probe and (2) a second group of plural reception signals received in response to a second ultrasonic wave transmitted from the ultrasonic probe, wherein a first sound field of the first ultrasonic wave is adjacent to or partially overlapped with a second sound field of the second ultrasonic wave,
performing filter processing on each of plural first reception signals of the first group of plural reception signals using a synthesized signal obtained by synthesizing plural second reception signals among the second group of plural reception signals to produce at least one filtered reception signal, the at least one filtered reception signal corresponding to at least one reception scanning line among plural first reception scanning lines corresponding to the plural first reception signals, and generating image data based on the at least one filtered reception signal, wherein the plural first reception scanning lines corresponding to the plural first reception signals are set at positions different from positions at which reception scanning lines corresponding to the plural second reception signals are set, wherein the performing the filter processing comprises performing, as the filter processing, weighted sum processing of weighting and summing each of the plural first reception signals and the synthesized signal; and wherein the performing the filter processing comprises determining a respective weight used for the weighted sum processing for each of the plural first reception signals based on an arrangement order of the plural first reception scanning lines corresponding to the plural first reception signals and a reception scanning line corresponding to the synthesized signal, or based on a distance between each of the plural first reception scanning lines corresponding to each of the plural first reception signals and the reception scanning line corresponding to the synthesized signal.

* * * * *